US011404645B2

(12) United States Patent
Yersin et al.

(10) Patent No.: US 11,404,645 B2
(45) Date of Patent: Aug. 2, 2022

(54) DIRECT SINGLET CAPTURE ORGANIC MOLECULES WITH SHORT EMISSION DECAY TIME AND APPLICATION THEREOF IN OPTOELECTRONIC DEVICES

(71) Applicant: SICHUAN KNOWLEDGE EXPRESS INSTITUTE FOR INNOVATIVE TECHNOLOGIES CO., LTD, Sichuan (CN)

(72) Inventors: Hartmut Yersin, Sinzing (DE); Larisa Mataranga-Popa, Regensburg (DE); Rafal Czerwieniec, Obertraubling (DE)

(73) Assignee: SICHUAN KNOWLEDGE EXPRESS INSTITUTE FOR INNOVATIVE TECHNOLOGIES CO., LTD, Meishan (CN)

( * ) Notice: Subject to any disclaimer, the term of this patent is extended or adjusted under 35 U.S.C. 154(b) by 453 days.

(21) Appl. No.: 16/341,875

(22) PCT Filed: Jan. 10, 2018

(86) PCT No.: PCT/CN2018/072034
§ 371 (c)(1),
(2) Date: Apr. 12, 2019

(87) PCT Pub. No.: WO2018/137494
PCT Pub. Date: Aug. 2, 2018

(65) Prior Publication Data
US 2019/0245151 A1 Aug. 8, 2019

(30) Foreign Application Priority Data

Jan. 25, 2017 (DE) .................... 10 2017 101 432.2
May 11, 2017 (EP) ..................... 17170682

(51) Int. Cl.
*H01L 51/00* (2006.01)
*C07D 219/02* (2006.01)
(Continued)

(52) U.S. Cl.
CPC ........ *H01L 51/0071* (2013.01); *C07D 219/02* (2013.01); *C07D 487/08* (2013.01);
(Continued)

(58) Field of Classification Search
None
See application file for complete search history.

(56) References Cited

U.S. PATENT DOCUMENTS

2016/0322567 A1* 11/2016 Li .................. H01L 51/0059
2018/0219159 A1 8/2018 Yersin et al.

FOREIGN PATENT DOCUMENTS

JP 2010-024149 A 2/2010
WO 2016/102413 A1 6/2016
WO 2017/017205 A1 2/2017

OTHER PUBLICATIONS

Machine English translation of Hayakawa et al. (JP 2010-024149 A). May 17, 2021.*
(Continued)

*Primary Examiner* — Jay Yang
(74) *Attorney, Agent, or Firm* — Maschoff Brennan

(57) ABSTRACT

The invention relates to novel pure organic emitter molecules and optoelectronic devices containing these organic emitter molecules. According to the invention, in the optoelectronic device, after the excitation of an organic molecule, relaxation and intersystem crossing processes also result from the almost isoenergetic charge transfer triplet state ($^3$CT) for the direct rapid occupation and emission of the charge transfer singlet state ($^1$CT), so that a $^1$CT→$S_0$ fluorescence occurs without a thermal activation.

20 Claims, 9 Drawing Sheets

(51) Int. Cl.
*C07D 487/08* (2006.01)
*C09K 11/06* (2006.01)

(52) U.S. Cl.
CPC .......... *C09K 11/06* (2013.01); *H01L 51/0051* (2013.01); *H01L 51/0052* (2013.01)

(56) References Cited

OTHER PUBLICATIONS

Extended European Search Report dated Nov. 28, 2017 as received in Application No. 17170682.3.

* cited by examiner

HOMO  LUMO

HOMO    LUMO

HOMO    LUMO

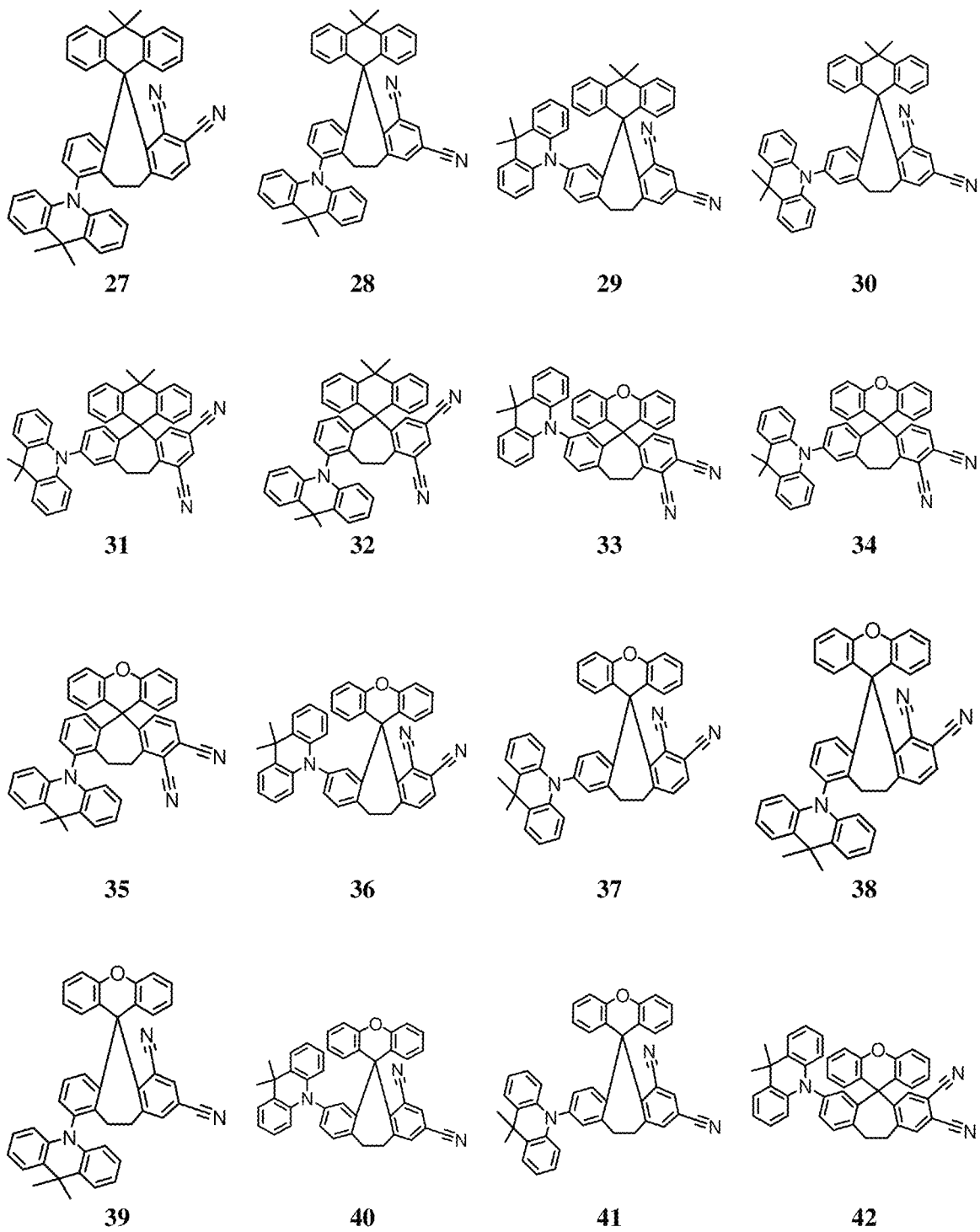

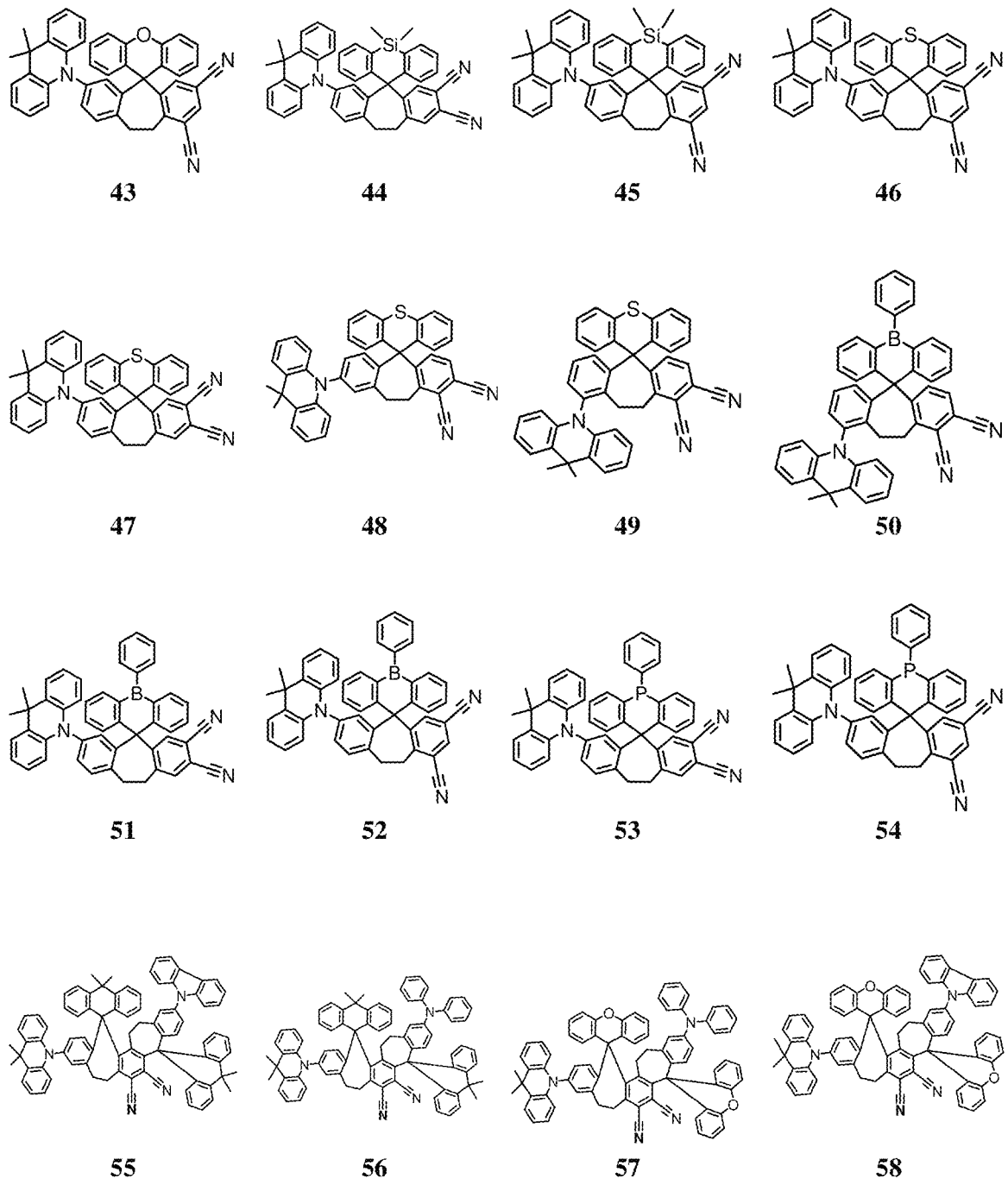

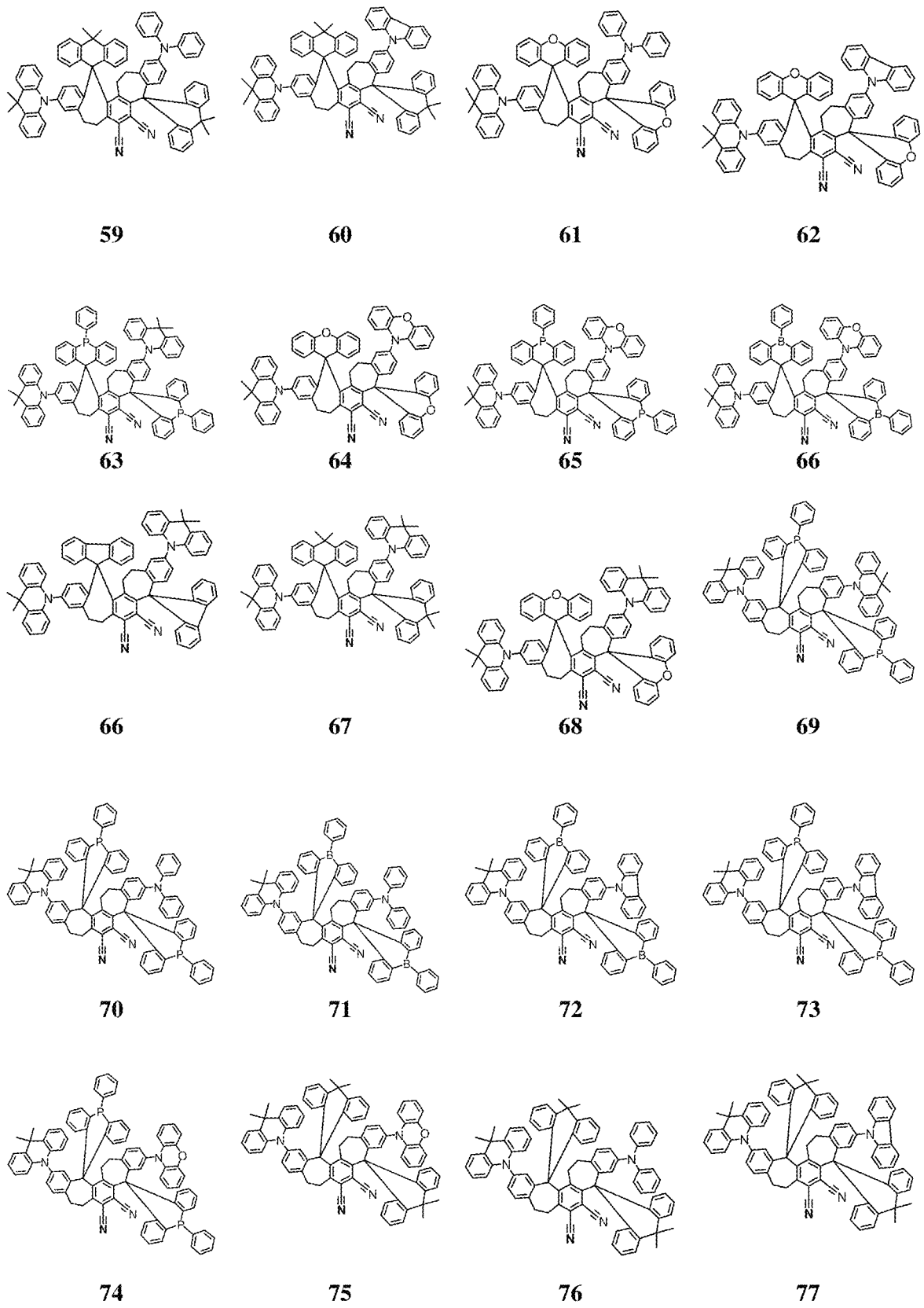

DIRECT SINGLET CAPTURE ORGANIC MOLECULES WITH SHORT EMISSION DECAY TIME AND APPLICATION THEREOF IN OPTOELECTRONIC DEVICES

The invention relates to organic molecules and their use in opto-electronic devices. These organic molecules have a donor and acceptor moiety linked by two organic non-conjugated bridges. The bridges show a reduced hyperconjugation. Thus singlet-triplet energy gap of only a few meV can be achieved. This allows 100% exciton usage in OLEDs with a short emission decay time. This new mechanism represents direct singlet harvesting, which is particularly suitable for use in opto-electronic devices. In contrast to the already known according to the state of the art, which is caused by a greater energy gap $\Delta E$ ($^1CT$-$^3CT$) in the order of several 100 cm$^{-1}$ (some 10 meV), singlet harvesting effect with a strongly temperature-dependent thermally activated delayed fluorescence (TADF) takes place in direct singlet-harvesting effect with the intersystem crossing between nearly iso-energetic $^3CT$ and $^1CT$ states with $\Delta E$ ($^1CT$-$^3CT$) values in the order of 10 cm$^{-1}$ (0.12 meV). In these molecules, the processes of occupation of $^1CT$ state proceed quickly so that the emission decay from this $^1CT$ states is in particular five to ten times faster than the molecules that exhibit TADF.

BACKGROUND

Figure 1:
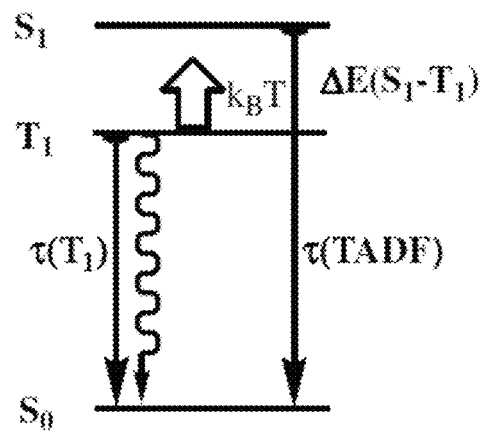

For luminescent molecules (emitter molecules) in opto-electronic applications, their emission decay time are required to be as short as possible, besides, they should also have a high emission quantum yield $\phi_{PL}$. Short emission decay times are important, for example, to achieve long OLED device life, which decreases the probability for chemical reactions (decompositions) of the emitter molecules in the excited state. Moreover, for such applications with purely organic emitter molecules, which are not metal-complex compounds, it is important to include the electronic occupation of the lowest excited triplet state $T_1$ in the emission process. This requirement can be satisfied by setting a sufficiently small energy gap $\Delta E$ ($S_1$-$T_1$) between the $T_1$ state and the overlying singlet state $S_1$, to allow a thermally activated delayed fluorescence (TADF) at room temperature (FIG. 1). This process is known to person skilled in the art (see, for example, B C A Parker, C G Hatchard, Trans. Faraday, Royal Society of Chem., 1961, 57, 1894) and is also referred to as E-type up conversion, first discovered for Eosin. As a result, an effective TADF is achievable that the decay time of the luminescence (emission) $\tau$ (TADF) is reduced by several orders of magnitude, compared with that of the phosphorescence $\tau$ ($T_1$) with the involvement of long-lived triplet state. Furthermore, in many cases, it can be achieved that the emission quantum yield $\phi_{PL}$ is increased significantly, because the non-radiative processes from the $T_1$ state (shown in FIG. 1) are less important, compared with the competing faster return cast process $T_1 \rightarrow k_B T \rightarrow S_1$.

It is known from the prior report that many molecules with intramolecular charge transfer (CT) transition between a donor (D) and an acceptor (A) segment may show TADF property. However, the energy gap $\Delta E(S_1$-$T_1)$ is still too large, and thus the photophysical properties required for many applications, such as a short decay without long decay foothills are not achievable.

DESCRIPTION

Surprisingly, it has now been able to find a method (molecular structural principle) which allows to reduce the energy gap $\Delta E(S_1$-$T_1)$ selectively to provide corresponding pure organic molecules. This energy gap is approximately proportional to the quantum mechanical exchange integral according to equation (1)

$$\Delta E(S_1-T_1) \approx \text{const.} \cdot \langle \psi_D(r_1)\psi_A^*(r_2) | r_{12}^{-1} | \psi_D(r_2)\psi_A^*(r_1) \rangle \quad (1)$$

Herein, $r_1$ and $r_2$ are the electron coordinates; $r_{12}$ is the distance between the electron 1 and electron 2; $\psi_D$ is the wave function of the HOMO (highest occupied molecular orbital), extending mainly over the donor segment of the molecule; $\psi_A^*$ is the wave function of the LUMO (lowest unoccupied molecular orbital), extending primarily over the acceptor part of the molecule. Based on the equation (1) it is apparent that $\Delta E(S_1$-$T_1)$ is small when the product of the wave functions $[\psi_D(r_1)\psi_A^*(r_2)]$ is small. This requirement can not be reached for a variety of molecules with intramolecular CT transitions because spatial extension of the wave functions $\psi_D(r_1)$ and $\psi_A^*(r_2)$ overlaps, resulting in large $\Delta E(S_1$-$T_1)$ values. According to the invention, molecular structures are proposed which markedly reduced superposition of the wave functions. This is achieved by molecular structures in which the donor or acceptor moieties are separated by non-conjugated small chemical groups (bridges). As a result, the extension of the HOMO into the acceptor region and the LUMO into the donor region are greatly reduced. Moreover, by chemical reinforcement of one or both bridges, it is possible to reduce the flexibility of the donor and the acceptor part. This makes it possible to increase the emission quantum yield and to reduce the $\Delta E(S_1$-$T_1)$ values and inhomogeneity of the emitter molecules.

In the molecules of the invention with extremely reduced overlaps of the wave functions, the hyperconjugations presented in the non-conjugated small chemical groups (bridges) (known to a person skilled in the art) are reduced by substitutions. This further reduces the extent of the HOMO into the acceptor region and the LUMO into the donor region.

The molecules of the invention are usually present in optoelectronic devices with other molecules, eg., evaporated with other small molecules or doped in polymers. These are referred to herein as matrices or matrix materials. The molecules of the invention can also be dissolved, and the solvent is then being the matrix. The energy levels of the molecules of the invention, which are incorporated or dissolved in such matrix materials/environments, doped or dissolved, are influenced in different ways by the polarity of the matrix. This property is explained further below.

Formulas Ia and Ib show the structure motif of the organic molecules of the invention with two organic bridges between the donor and acceptor segments. By suitable selection of these bridges, the spatial overlap of HOMO (predominantly lying on the donor) and LUMO (predominantly on the acceptor) can be significantly reduced, by largely suppressing the hyperconjugation by substitution (s) in one or both bridges. A remaining slight overlap of orbitals is, however, useful in order not to make the transition probability between the electronic ground state $S_0$ and the excited $S_1$ state ($^1CT$-state) be too small [R. Czerwieniec et al., Coord. Chem. Rev. 2016, 325, 2-26]. In addition, the two-bridges lead to stiffening of the molecule. This results in an increase in the emission quantum yield as well as a reduction in the emission half-value range. In many cases, the latter is useful to achieve a desired emission color (color purity) for the light generation in OLEDs. Furthermore, the occurrence of the long-lived tails of the emission decay curves is largely suppressed.

The Formulas Ia and Ib show structural motifs of the organic molecules of the invention consisting of an aromatic or a heteroaromatic donor segment D, D1, D2 and an aromatic or a heteroatom which is bonded via two or four non-conjugated bridges B1, B2, B3 and B4, and aromatic acceptor segment A. The aromatic or heteroaromatic moieties are substituted with electron-withdrawing substituents and thereby become donors and acceptors, respectively. Exemplary embodiments are given below. The bridges are selected in such a way that they prevent pronounced overlaps of the donor HOMO with the acceptor LUMO. The bridge B2 and/or the bridge B3 can, for example, have an aromatic or heteroaromatic unit. In particular, the bridges have a reduced hyperconjugation compared to the prior art. This results in a substantially smaller energy difference $\Delta E(^1CT\text{-}^3CT)$, as will be explained further below.

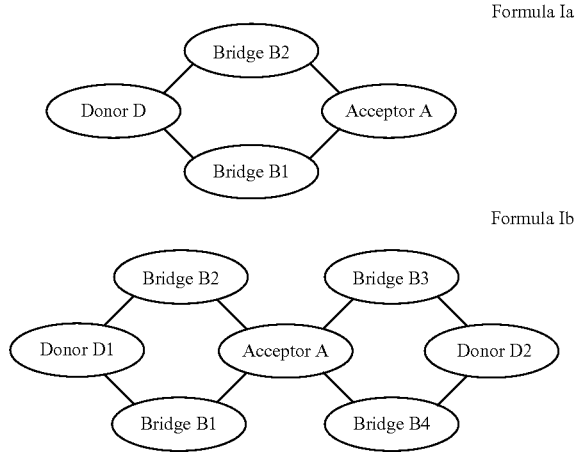

Formula Ia

Formula Ib

For optoelectronic applications with a request of a small $\Delta E(S_1\text{-}T_1)$ value, it is important that the energy gap between the HOMO localized on the donor and the acceptor localized on the LUMO is in the range between 1.8 and 3.3 eV, thus allow the energy of the HOMO→LUMO transition to be in the visible region. The energy levels of HOMO and LUMO can be described by the strengths of the electron-donating (for the donors) or the electron-withdrawing (for the acceptors) effects. These terms are known to a person skilled in the art and are also described below in concrete embodiments.

In the invention, the energy gap $\Delta E(S_1\text{-}T_1)$ of molecules is less than 20 cm$^{-1}$ (2.5 meV), more preferably less than 10 cm$^{-1}$ ($\approx$1.2 meV). Thus, the singlet and triplet states of charge transfer in comparison to the present at room temperature the thermal energy $k_B T = 210$ cm$^{-1}$ are substantially isoenergetic. Detailed instructions on the molecular structure are given below. The corresponding value is determined by the individual molecule. It can be determined by quantum mechanical calculations, for example, using TD-DFT programs (eg. with the Gaussian 09 program, especially when using an MO6 functional) or the freely available NWChem version (eg Version 6.1), the CC2 method (TURBOMOLE GmbH, Karlsruhe) or a CAS method (Complete ActiveState method). [See, e.g., B D I Lyakh, M. Musiaz, V F Lotrich, R J Bartlett, Chem. Rev. 2012, 112, 182-243 and P G Szalay, T. Muller, G. Gidofalvi, H. Lischka, R. Shepard, Chem. Rev. 2012, 112, 108-181]. Exemplary embodiments are given below.

The emission decay time $\tau$ (300 K) should be less than 2 microseconds, better less than 1 microseconds for practical applications,. To achieve this, in addition to the adjustment of a small $\Delta E(S_1\text{-}T_1)$ value, it may be useful to tune the spin-orbit interaction (SBK, SOC) between the $T_1$ state and higher molecular energy states, in order to obtain a larger intersystem crossing (ISC) rate. For this purpose, for example, a substitution of the donor segment D and/or the acceptor segment A and/or one or both bridges with a halogen Cl, Br and/or I is suitable.

An increase in the rate of ISC for the inventive molecules is also achieved by the CT states energetically closely spaced to the donor D and/or acceptor A and/or one or both bridges lying localized triplet states $^3$LE (LE=excited localized). The increase in ISC rate between $^1$CT and $^3$CT states is given by a reinforcement of the spin-orbit interaction due to quantum mechanical mixtures between these states and the $^3$LE states. The target molecules are determined by using known computer programs or quantum mechanical methods (eg Gaussian 09 or CC2 method). These mixtures more effective and the closer states are energetically adjacent. A mutual energetic shift can be achieved by means of changes in the donor and/or acceptor strengths as well as changes in electron-donating substitutions on the donor and/or changes in electron-accepting substitutions at the acceptor. Also, by using more than one electron-pushing and/or pulling substitutions, an energetic shift can be achieved. Importantly, in one embodiment of the invention, a matrix with suitable polarity can be used. As a result, the blank, $^1$CT and $^3$CT states, in contrast to $^3$LE states move energetically (if the organic molecule does not have the desired sequence of states), so that the $^{1,3}$CT-states are below or lie only slightly above the $^3$LE-conditions. The polarity of the matrix can be described by the dielectric constant $\varepsilon$. (Values can be found in the respective literature tables). The influence of the polarity can also be detected by the above mentioned calculation programs.

The influence of the polarity of the matrix, for example, the solvent, will be explained with reference to FIG. 2. In this Figure, the red shift of the emission spectra is shown with increasing polarity of the solvent (quantified by the dielectric constant $\varepsilon$. The emission results from a molecule of the invention is described below (example molecule 1).

The organic molecules of the invention are constructed in such a way that $^1$CT and $^3$CT-conditions are below the $^3$LE states, for example, less than 1500 cm$^-$($\approx$190 meV), preferably less than 500 cm$^{-1}$ ($\approx$63 meV) or more preferably less than 100 cm$^{-1}$ ($\approx$12 meV). An energetic position of the $^3$LE-conditions slightly below the $^1$CT and $^3$CT-conditions (eg., 50 cm$^{-1}$≈6 meV) is also possible. The corresponding energy gaps can be determined by quantum-theoretical TD-DFT calculations. Moreover, it can be experimentally determined whether the localized $^3$LE state is energetically below the $^{1,3}$CT-states by recording low-temperature emission spectra (eg. at 77 K or 10 K). In this case, the emission is structured so that vibration satellites can be resolved. In addition, the emission decay time of the emitting $^3$LE state, which is in the range of ms to s, is significantly longer than the $^1$CT-decay time (<2 microseconds). In the opposite case, broad CT spectra is found with half-widths of several thousand cm$^{-1}$ and short decay time.

The chemical bonding between the donor and acceptor segments of the organic molecule not only have the effect of stiffening of the molecule, but also surprisingly lead to an increase of the emission quantum yield $\phi_{PL}$.

In addition, the bridges cause a strong restriction on the free mobility of the donor molecule segment D and the acceptor molecule segment A of the organic molecule. The long-term emission decay time often encountered in the prior art, are significantly reduced in the region of the long-lived "decay tails". An improvement in the color purity of the emission is also achieved by reducing the half-width of the emission band.

Surprisingly, the molecules of the invention (optionally together with a matrix having a polarity, described by the dielectric constant in the range of 2.4≤ε≤5.0), which show the effective ISC and a very small energy gap ΔE($^1$CT-$^3$CT) less than 20 cm$^{-1}$ (2.5 meV), preferably less than 10 cm$^{-1}$ (≈1.2 meV), only give a $^1$CT-fluorescence, without a time delayed TADF emission. With a value of less than 2 μs to less than 500 ns, this is clearly more short-lived than that of the prior art TADF emitters. The organic molecules of the invention, possibly together with a matrix as a composition or combination, which are used as emitters in OLEDs, can collect all the singlet and triplet excitons in the singlet charge-transfer state, in a time window which is within the decay time of the fluorescence. It is a "Direct Singlet Harvesting Effect". As a result, the emitter-matrix combinations of the invention show only the short decay times of the fluorescence, and the energy gap is only a few hundred ns to 1 or 2 μs. This fluorescence is equilibrated with the nearly iso-energetic $^3$CT-state fluorescence from the $^1$CT-singlet state. In contrast to the known singlet harvesting effect with a strongly temperature dependent thermally activated delayed fluorescence (TADF) (caused by a greater energy difference ΔE($^1$CT-$^3$CT) in the range of some 10$^2$ cm$^{-1}$), "Direct Singlet Harvesting Effect" takes place between the ISC nearly iso-energetic $^3$CT and $^1$CT states. In these molecules, optionally in combination with a matrix, the processes fill the $^1$CT-state quickly so that the emission decay from these $^1$CT states in particular is five to ten times shorter than TADF molecules.

Description of the Molecular Structure of Formulas Ia and Ib

According to the formulas Ia and Ib, the molecular structure of the emitter materials in the invention is explained further by means of the formulas IIa to IIe. The concomitant use of polar matrices, with a dielectric constant (polarity) of 2.4≤ε≤4.5 in a composition comprising an organic molecule of the invention, can lead to further improvements in the direct singlet-harvesting effect (reduction of the $^1$CT-fluorescence decay time).

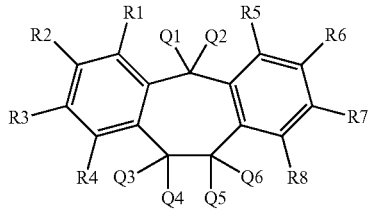

Formula IIa

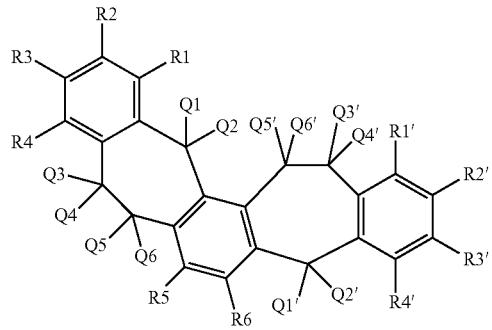

Formula IIb

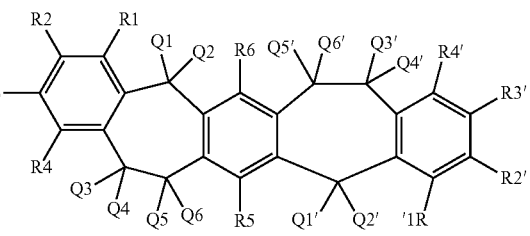

Formula IIc

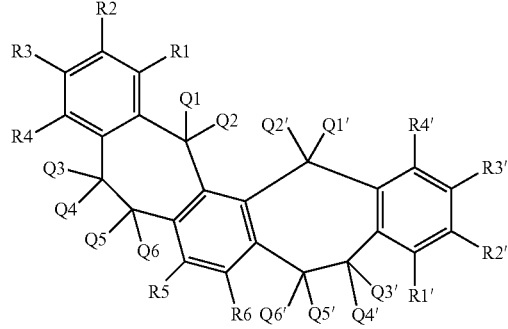

Formula IId

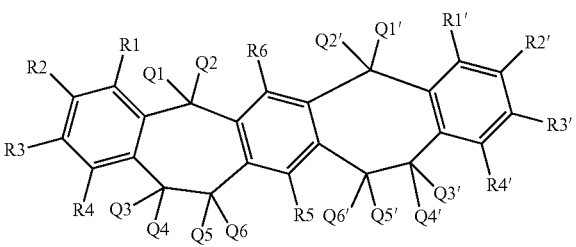

Formula IIe

According to the formulas IIa to IIe, the basic skeleton of the organic molecules in the invention is 2,3: 6,7-dibenzosuberan. By means of suitable substitutions shown here, the electronic properties of the aromatic ring systems are controlled. The molecule part substituted by R1 to R4 is the donor part D or the molecule parts substituted by R1 to R4 and R1' to R4' become donor parts D1 and D2 in the sense of the formulas Ia and Ib and the one with R5 to R8 or the molecule part substituted with R5 and R6 becomes the acceptor part A. The methylene and ethylene groups of the 2,3: 6,7-dibenzosuberane, which are substituted by Q1 to Q6, represent the bridges B1 and B2, respectively, and the methylene and ethylene groups substituted by and Q1' to Q6' of the 2,3: 6,7-dibenzosuberans represent the bridges B3 and B4 of the formulas Ia and Ib.

Bridges:

Q1, Q2, Q1' and Q2' are each independently selected from alkyl, alkenyl, alkynyl, cycloalkyl or aryl.

Q3 to Q6 and Q3' to Q6' are each independently selected from H, alkyl, alkenyl, alkynyl, cycloalkyl or aryl.

wherein:

Alkyl is a straight-chain (unbranched) or branched ($C_1$-$C_{10}$) alkyl having 1 to 10 carbon atoms in the main hydrocarbon chain (eg. Methyl, ethyl, n-propyl, i-propyl, n-butyl, i-Butyl, t-butyl, n-pentyl, etc.), Alkenyl is a straight or branched ($C_1$-$C_{10}$) alkenyl having 1 to 10 carbon atoms in the main hydrocarbon chain (eg. propen-2-yl, n-buten-2-yl, n-buten-3-yl), Alkynyl is a straight or branched ($C_1$-$C_{10}$) alkynyl, having 1 to 10 carbon atoms in the main hydrocarbon chain (eg. propen-2-yl, n-buten-2-yl, n-buten-3-yl), Cycloalkyl is a ($C_1$-$C_{10}$)-cycloalkyl having 3 to 7 ring carbon atoms, and Aryl is a 5-membered or 6-membered aromatic or heteroaromatic group, benzene, thiophene, furan, imidazole, azole, diazole, triazole, tetrazole, oxazole, etc.

"Main hydrocarbon chain" means the longest chain of the branched or non-straight-chain alkyl, alkenyl or alkynyl.

Each group of Q1 to Q6 and Q1' to Q6' can be substituted or unsubstituted by one or more F, Cl, Br, alkoxy, thioalkoxyl, amine, silane, phosphane, borane or aryl.

The groups Q1 and Q2, the groups Q3 and Q4, the groups Q5 and Q6, the groups Q1' and Q2', the groups Q3' and Q4', as well as the groups Q5' and Q6', may be chemically linked to each other, to further form ring systems.

Donors:

R1-R4 and R1' to R4' are each independent selected from H, alkyl, alkenyl, alkynyl, cycloalkyl, alkoxyl, thioalkoxyl, amine, phosphane, silane, borane, fluorine, chlorine, bromine or the group Akr defined below by formula III. In formula IIa, at least a position from R1 to R4 is Akr and in the formulas IIb to IIe at least a position from R1 to R4 and at least one position from R1' to R4' is Akr.

wherein:

Alkyl is a straight or branched ($C_1$-$C_{10}$) alkyl (eg. Methyl, ethyl, n-propyl, i-propyl, n-butyl, i-butyl, t-butyl, n-pentyl, etc.), which has 1 to 10 carbon atoms in the main hydrocarbon chain, Alkenyl is a straight or branched ($C_1$-$C_{10}$) alkenyl (eg. propen-2-yl, n-buten-2-yl, n-buten-3-yl) containing 1 to 10 carbon atoms in the main hydrocarbon chain having, Alkynyl is a straight or branched ($C_1$-$C_{10}$) alkynyl (eg. propen-2-yl, n-buten-2-yl, n-buten-3-yl) containing 1 to 10 carbon atoms in the main hydrocarbon chain having, Cycloalkyl is a ($C_3$-$C_7$)-cycloalkyl having 3 to 7 ring carbon atoms, and Aryl is a 5-membered or 6-membered aromatic or heteroaromatic group, benzene, thiophene, furan, imidazole, azole, diazole, triazole, tetrazole, oxazole, etc.

The alkoxyl, thioalkoxyl, amine, phosphane, silane and borane substitutions are each an alkoxyl OR', thioalkoxyl SR', amine NR'R'', phosphane PR'R'', silane SiR'R''R''' and borane BR'R'', where R', R'' and R''' are each independent selected from a straight or branched ($C_1$-$C_{10}$) alkyl, ($C_1$-$C_{10}$) alkene, ($C_1$-$C_{10}$) alkyne, ($C_3$-$C_7$) cycloalkyl or a 5-ring or 6-membered aromatic or heteroaromatic group mean.

The group Akr consists of a structure of the formulas IIIa and IIIb:

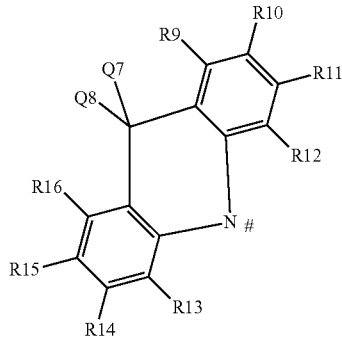

Formula IIIa

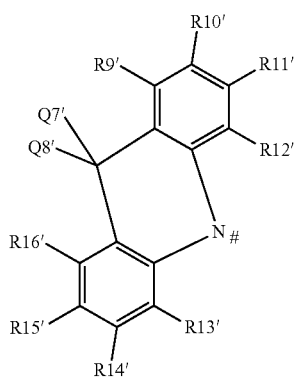

Formula IIIb wherein:

marks the site through which the Akr group is attached to the rest of the molecule, R9 to R16 and R9' to R16' are independently selected from H, ($C_1$-$C_{10}$)-alkyl, ($C_1$-$C_{10}$)-alkenyl, ($C_1$-$C_{10}$)-alkynyl, ($C_3$-$C_7$)-Cycloalkyl, alkoxyl OR', amine NR'R'', phosphane PR'R'', silane SiR'R''R''', borane BR'R'', fluorine, chlorine, bromine or aryl, where radicals R', R'' and R''' is independently straight or branched ($C_1$-$C_{10}$)- alkyl, ($C_1$-$C_{10}$)-alkene, ($C_1$-$C_{10}$)-alkyne, ($C_1$-$C_{10}$)-cycloalkyl or a 5-ring or 6-membered aromatic or heteroaromatic group;

Q7, Q8, Q7' and Q8' are defined as Q1 to Q6 and Q1' to Q6' and may be linked to each other or further form a ring system.

Acceptor:

R5 to R8 are independently H, $CH_3$, CN, COR', CO (OR'), CO (NR'R''), $SO_2R'$, $SO_2(OR')$, SOR', $CF_3$, $CF_2R'$, in which R' is as defined above. At least one group is not H or $CH_3$.

Furthermore, at least two substituents selected from R5, R6, R7 and R8 are not H or $CH_3$ in the formula IIa, preferably.

In one embodiment of the molecules of the invention, two adjacent groups selected from R5, R6, R7 and R8 may be chemically linked to each other. Such linkages, which results in a stiffening effect of the molecular structure, as well known to a person skilled in the art, can lead to an increase in the emission quantum yield.

In one embodiment of the molecules according to the invention, hydrogen atoms can be replaced by deuterium at one, several or all positions in the molecule of the formula IIa to IIe according to the invention, in order to increase the emission quantum yield.

In a further embodiment, the molecule has a structure of Formulas IVa to IVd according to the invention.

Formula IVa
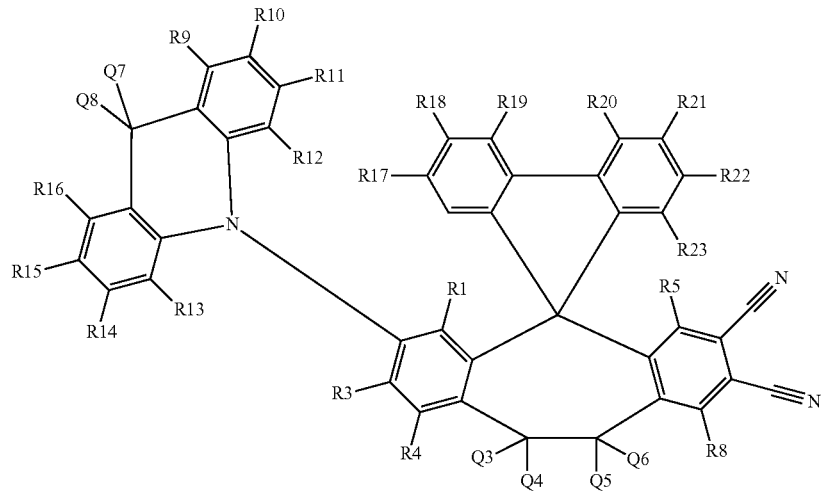
Formula IVb
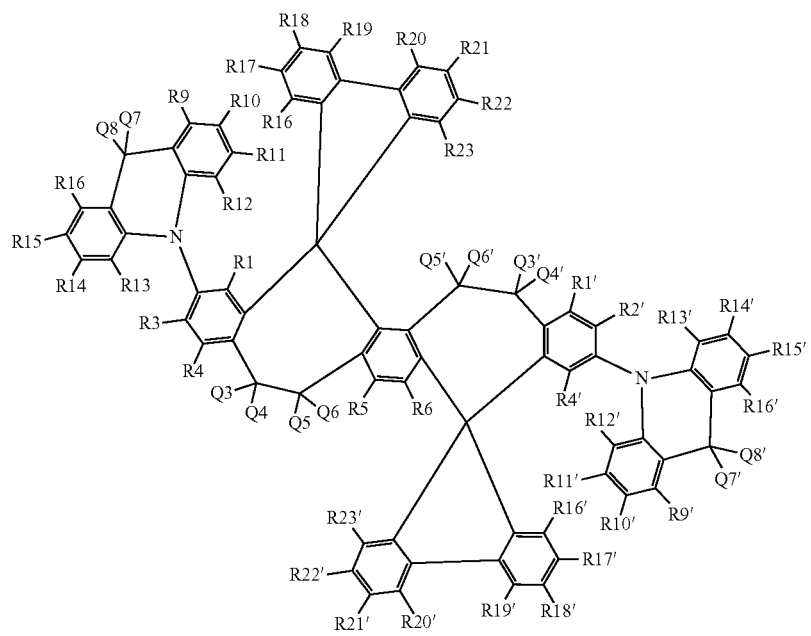

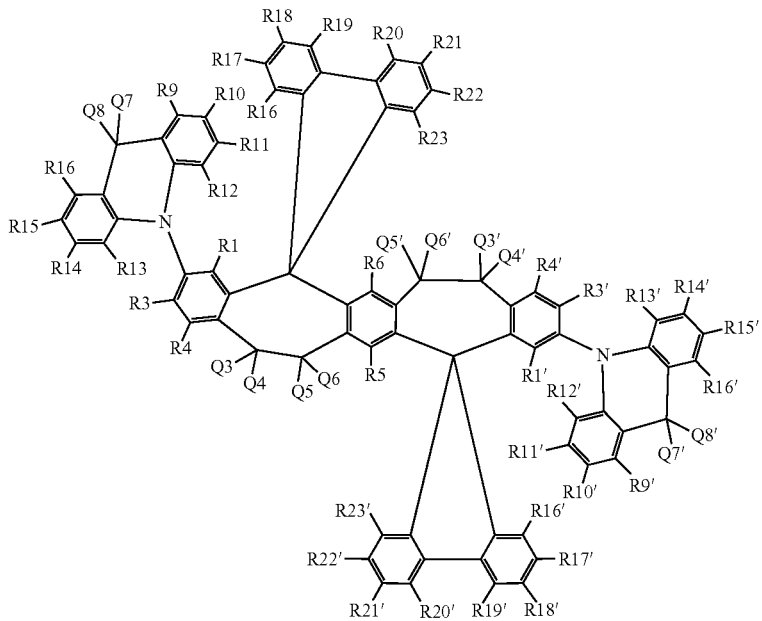
Formula IVc
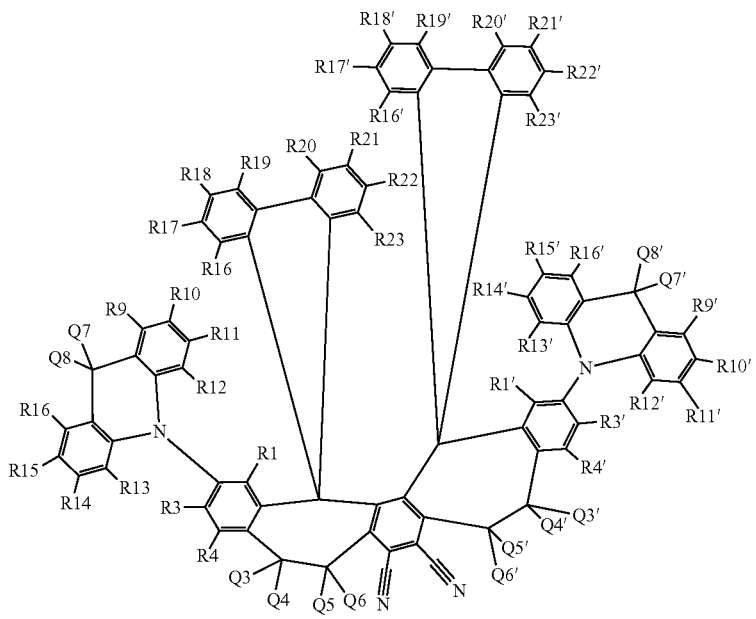
Formula IVd
The substituents R1 to R8, R1' to R8', Q3 to Q6 and Q3' to Q6' are described under the Formulas IIa to IIe and the substituents R9 to R16 and Q7 to Q8 are described under the Formulas IIIa and IIIb. R16 to R23 and R16' to R23' are defined as R9 to R16 and R9' to R16'.
In a further preferred embodiment, the organic molecule has a structure of Formula V according to the invention.

Formula V

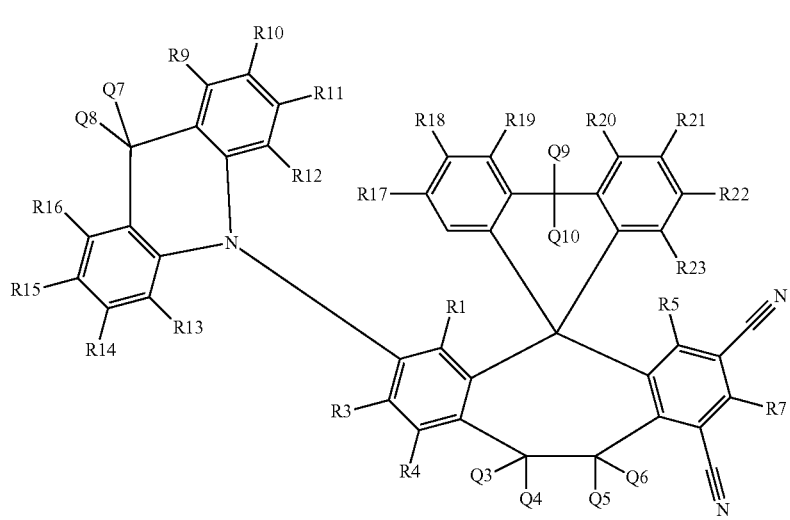

The substituents R1 to R23 and Q3 to Q8 are explained under the formulas IIa to IIe, III, IIIb and IVa to IVd.

Q9 and Q10 are defined as Q1 to Q8 and Q1' to Q8' and may be linked to each other, so that a ring system is further formed.

In a further preferred embodiment, the organic molecule has a structure of formula VI according to the invention.

Formula VI

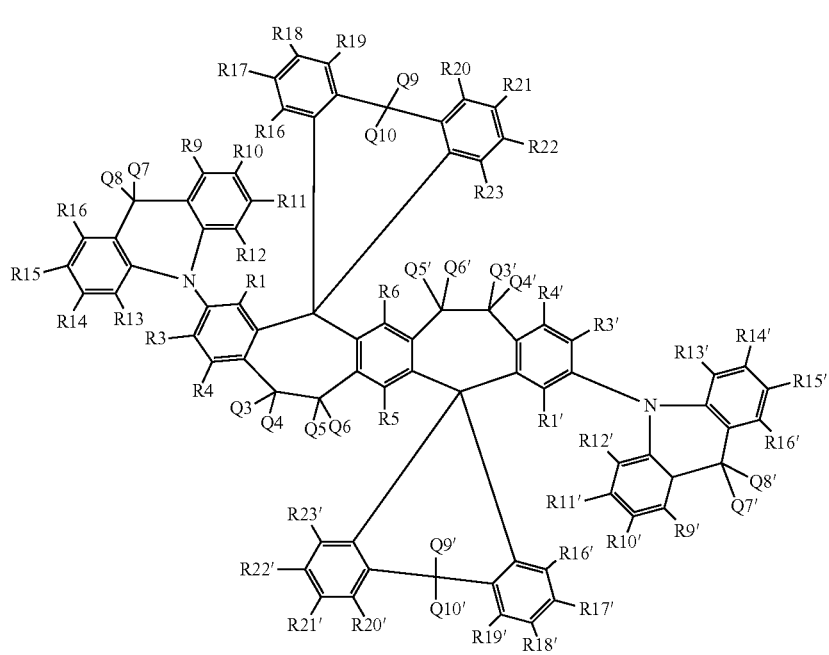

The substituents R1 to R23, R1' to R23', Q3 to Q10 and Q3' to Q8' are explained under the formulas IIa to IIe, III, IIIb, IVa to IVd and V.

Q9' and Q10' are defined as Q1 to Q10 and Q1' to Q8' and may be linked to one another, so that a ring system is further formed.

In further preferred embodiments, the organic molecule has structures of the Formulas VII to XVI according to the invention.

Formula VII
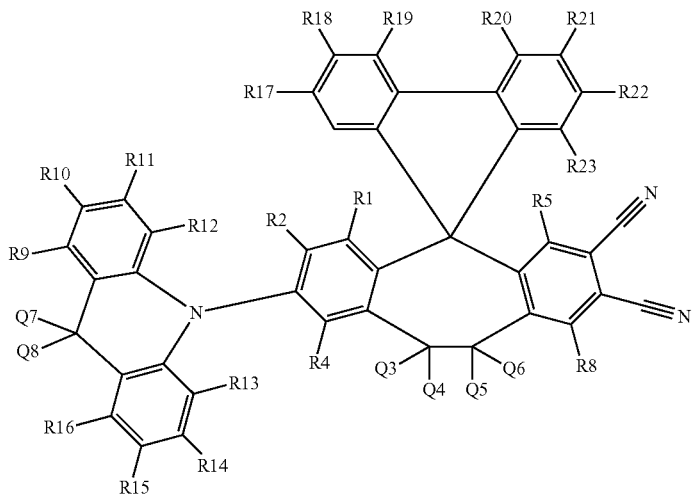
Formula VIII
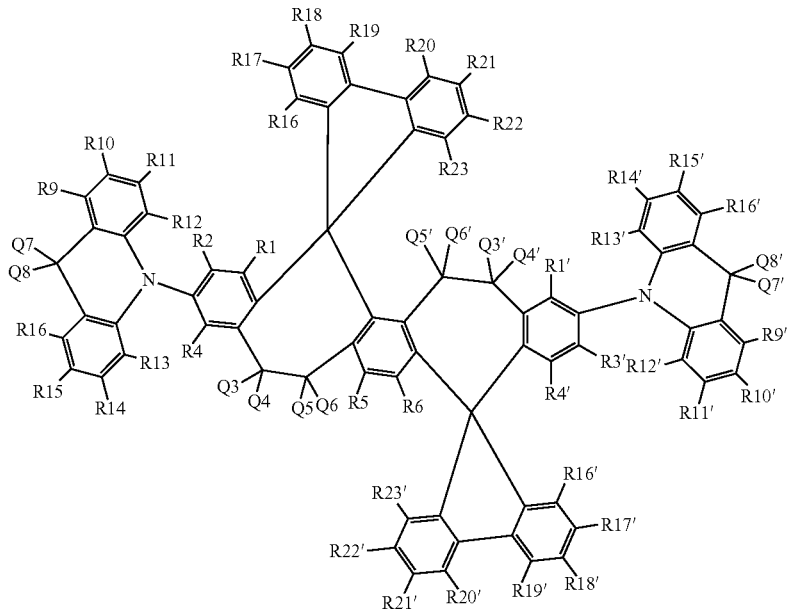
Formula IX
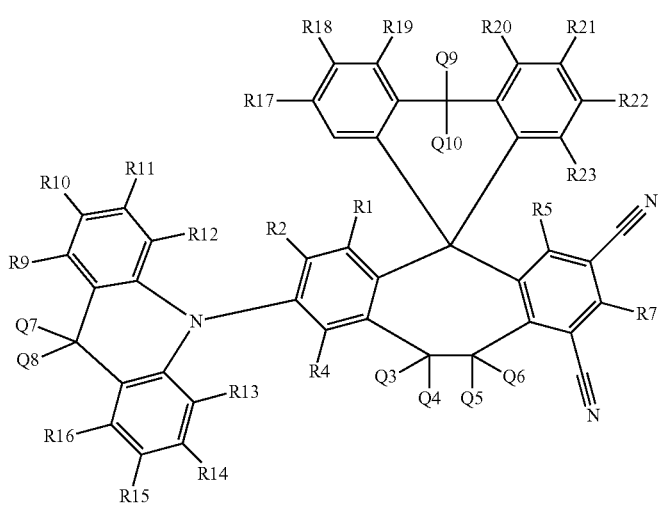

Formula X
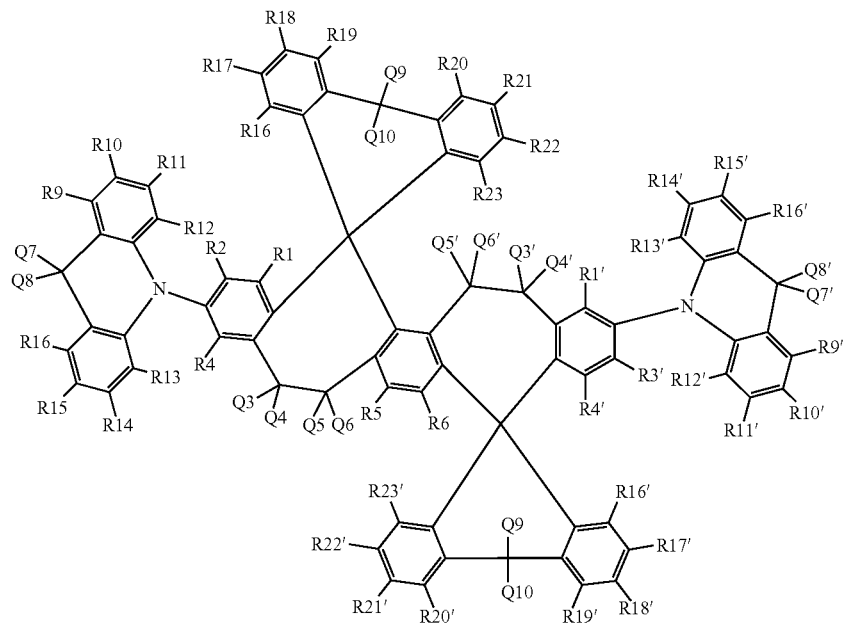
Formula XI
Formula XII
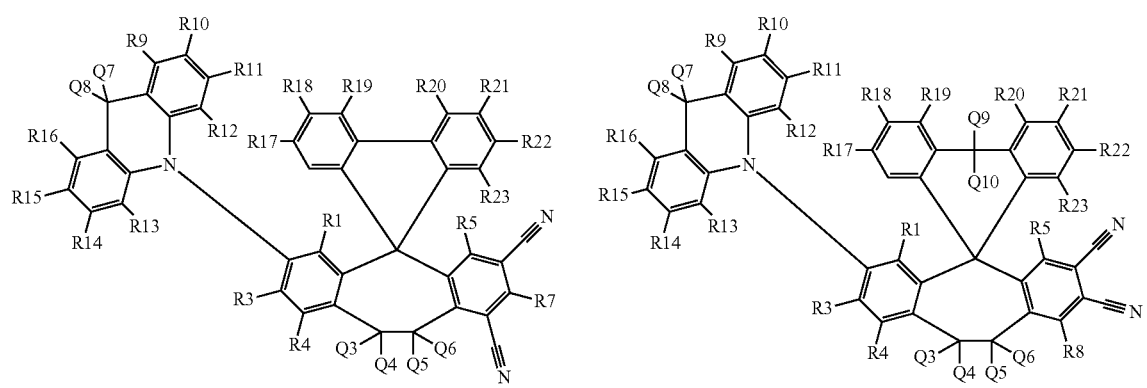
Formula XIII
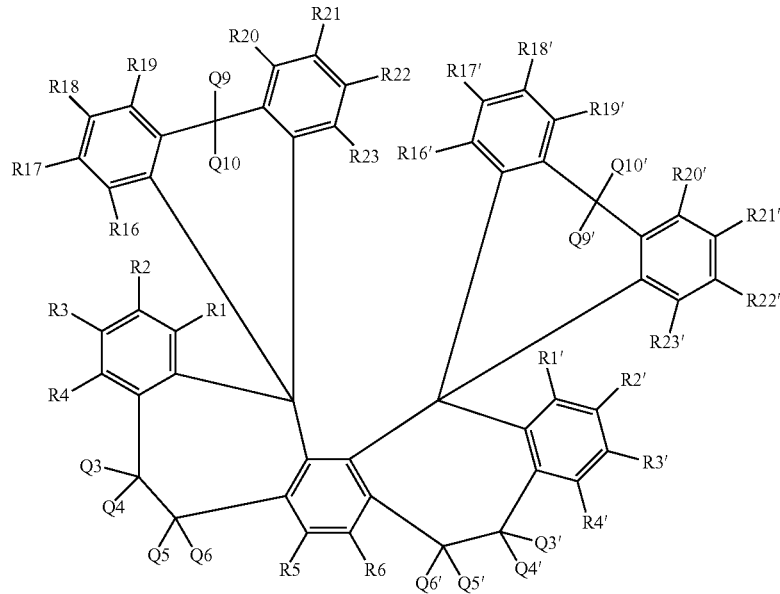

-continued

Formula XIV

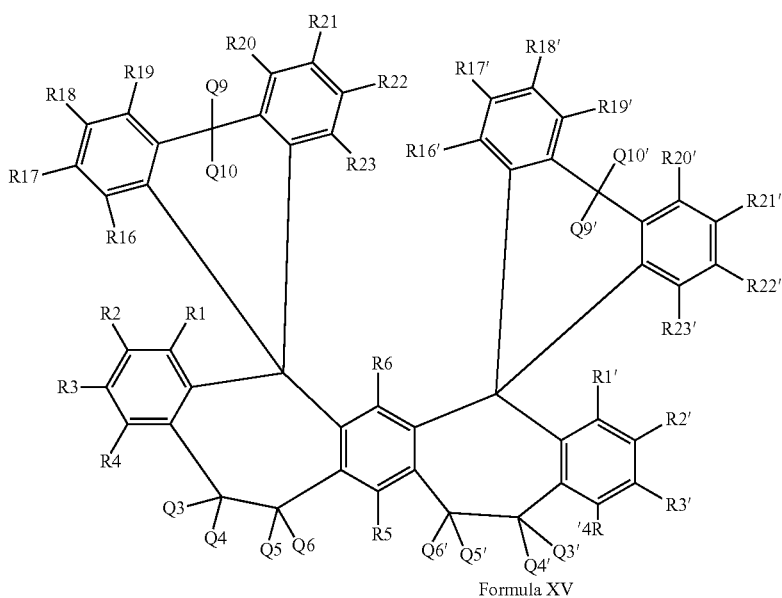

Formula XV

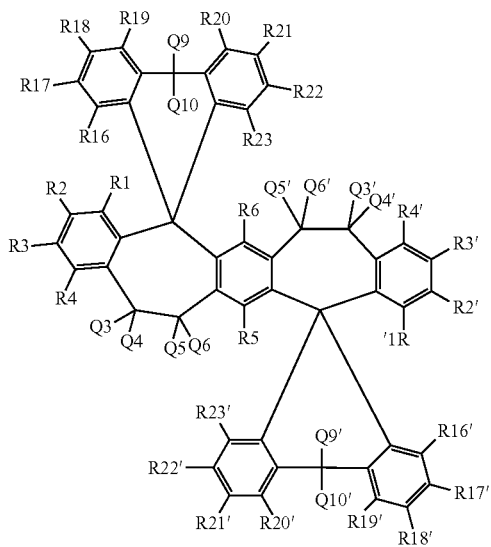

Formula XVI

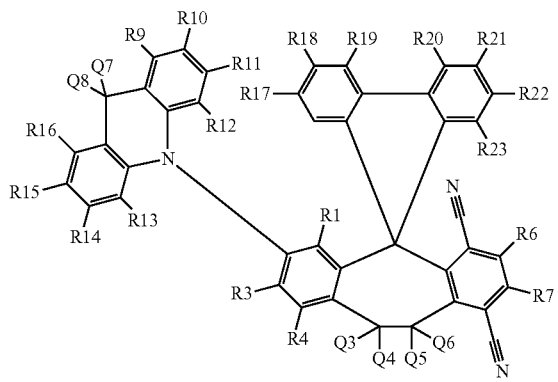

The above mentioned definitions apply.

EXAMPLES

The organic molecules presented in the invention, which may be part of a composition or combination with a matrix material, can be synthesized through known catalytic coupling reactions (eg, Suzuki coupling reaction, Buchwald-Hartwig cross-coupling reaction).

The organic molecules (emitter molecules) have an energy gap between the charge-transfer conditions $\Delta E(^1CT-^3CT)$, which is less than 20 cm$^{-1}$ (2.5 meV), preferably less than 10 cm$^{-1}$ ($\approx$1.2 meV). In contrast to the previous technology, this small difference in energy is achieved by an bridge(s), in which existing Hyper-Conjugation is significantly reduced by substitution(s) at the $C_1$-bridge B2 and B3. The structure motif is illustrated here:

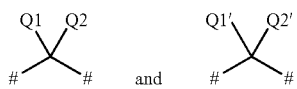

in which

\# marks the position in which the carbon atom or the spiro carbon atom of the bridge B2 or B3 is connected to the donor or acceptor fragment in the molecule of the formula Ia or Ib. Furthermore: Q1, Q2, Q1' and Q2' ≠H.

The emitter molecules are in a solid matrix (e.g. in OLEDs) and thus represent the emission layer. The polarity of the matrix is selected so that the localized $^3$LE states are energetically above the $^{1,3}$CT states, for example, less than 1500 cm$^{-1}$ ($\approx$190 meV) or preferably less 500 cm$^{-1}$ ($\approx$63 meV), more preferably less than 100 cm$^{-1}$ ($\approx$12 meV). On the other hand, the $^3$LE state may be 50 cm$^{-1}$ ($\approx$6 meV)

below the $^{1,3}$CT states. The matrix polarity can be selected, for example, in terms of the dielectric constant ε, in the range of $2.2 \leq \varepsilon \leq 5.0$.

Example 1

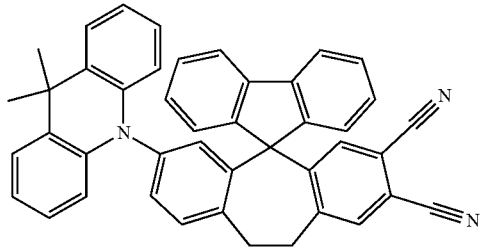 [SMILES: CC1(C)c2ccccc2N(c2ccc3c(c2)C2(c4cc(C#N)c(C#N)cc4CC3)c3ccccc3-c3ccccc32)c2ccccc21]

Example Molecule 1

Hereinafter, the molecule shown in example 1 according to the invention is discussed in more detail.

Figure 3:
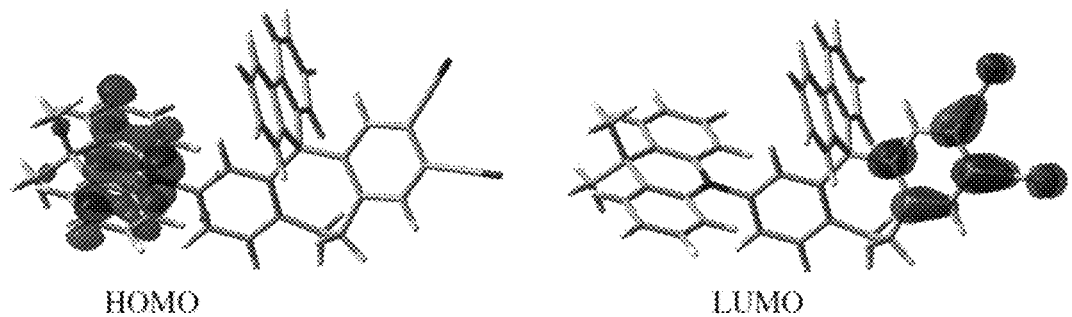

The frontier orbitals shown in FIG. 3 show that HOMO and LUMO are located in distinctly different regions of the molecule. This suggests that the energy splitting between the lowest triplet and the above singlet state is small. Calculation for the example molecule 1 in a TD-DFT calculation (Functional B3LYP and also Functional MO6) shows that the energy difference for the optimized triplet geometry ΔE ($^{1}$CT-$^{3}$CT)=7 cm$^{-1}$ (0.87 meV). Thus, example 1 represents an emitter molecule according to the invention, which is suitable for use in optoelectronic devices, such as OLEDs.

The chemical synthesis of the molecule example 1 started from commercially available materials is shown in the following scheme.

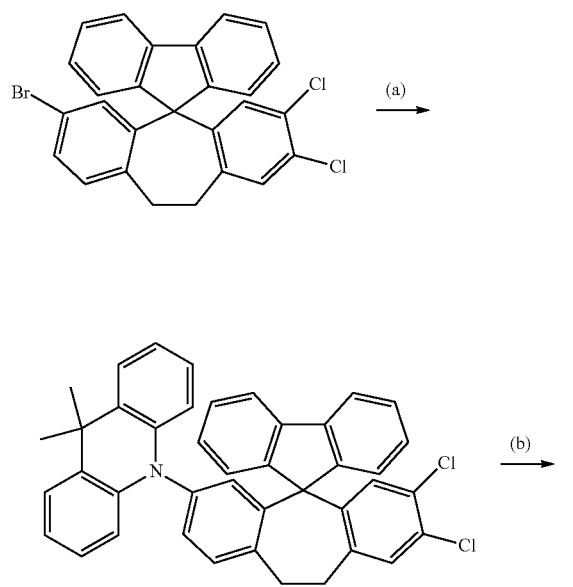

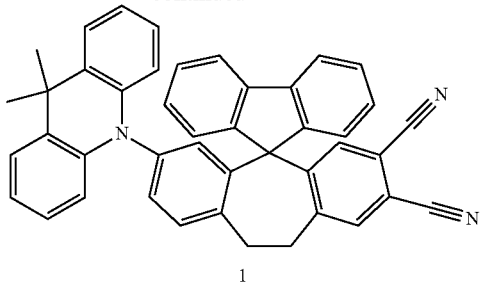

1

Reactants and reaction conditions: (a) 9,9-dimethyl-9,10-dihydroacridin, Pd(CH$_3$COO)$_2$, P[(C(CH$_3$)$_3$]$_3$, (CH$_3$)$_3$CONa, 90° C., 19 h. (b) Zn(CN)$_2$, 1,1'-bis(diphenylphosphino)ferrocene, [1,1'-bis(diphenylphosphino)ferrocene]dichlorpalladium(II) complex with dichloromethane, N-methyl-2-pyrrolidone, 180° C., 12 h.

Chemical Analysis:
$^{1}$H NMR (300 MHz, CDCl$_3$, δ): 7.71 (d, J=7.5 Hz, 2H), 7.66 (s, 1H), 7:34 (q, J=7.5 Hz, 6H), 7.22 (d, J=7.5 Hz, 1H), 7.11 (d, J=7.5 Hz, 2H), 6.92 (d, J=7.5 Hz, 1H), 6.80 (t, J=9 Hz, 3H), 6.71 (t, J=7.5 Hz, 2H), 6.32 (d, J=3 Hz, 1H), 5.72 (d, J=7.5 Hz, 2H), 3.48 (d, J=3.6 Hz, 4H), 1.53 (s, 6H). $^{13}$C NMR (75 MHz, CDCl$_3$, δ): 156.35, 148.69, 148.36, 140.53, 130.07, 129.22, 128.59, 126.07, 124.79, 124.67, 121.51, 120.43, 113.66, 66.47, 38.13, 36.73, 35.82, 30.49. MS (HR-ES-MS=high resolution electrospray mass spectrometry) m/z: C$_{44}$H$_{31}$N$_3$ gives: 601.2518; found 601.3514. C$_{44}$H$_{31}$N$_3$ results: C, 87.82; H, 5.19; N, 6.98, found: C, 87.48; H, 5.41; N, 6.60.

Figure 4:
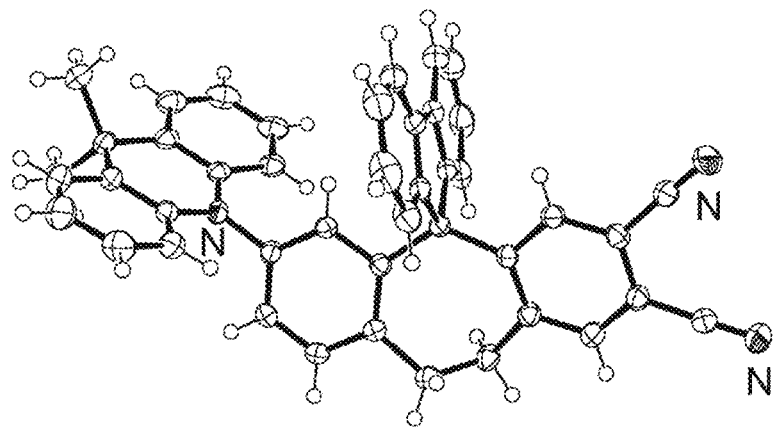

Crystal Structure:
FIG. 4 shows the molecular structure which results from an X-ray structure determination. Further structural data are summarized in Tables 1 and 2.

TABLE 1

X-ray diffraction data for the molecule of Example 1.

| | |
|---|---|
| Formula | C$_{44}$H$_{31}$N$_3$ |
| D$_{calc}$/G cm$^{-3}$ | 1.237 |
| μ/mm$^{-1}$ | 0.556 |
| Molar mass | 601.72 |
| Colour | yellow |
| Shape | irregular |
| Size/mm$^3$ | 0.21 × 0.20 × 0.14 |
| T/K | 123.00 (10) |
| crystal system | monoclinic |
| space group | P2$_1$/c |
| a/Å | 10.68690 (10) |
| b/Å | 12.46700 (10) |
| c/Å | 24.3981 (3) |
| a/° | 90 |
| b/° | 96.2130 (10) |
| g/° | 90 |
| V/Å$^3$ | 3231.55 (6) |
| Z | 4 |
| Z' | 1 |
| Wavelength/Å | 1.54184 |
| Radiation | CuK$_α$ |
| Θ$_{min}$/° | 3.645 |
| Θ$_{max}$/° | 73.424 |
| Measured reflections | 35409 |
| Independent reflections | 6430 |
| Used reflections | 5714 |
| R$_{int}$ | 0.0284 |
| Parameter | 426 |
| Restrictions | 0 |
| the biggest Peak | 0.229 |
| the deepest hole | −0.238 |
| GoF | 1.024 |

TABLE 1-continued

X-ray diffraction data for the molecule of Example 1.

| | |
|---|---|
| wR$_2$ (all data) | 0.1037 |
| wR$_2$ | 0.0988 |
| R$_1$ (all data) | 0.0438 |
| R$_1$ | 0.0388 |

TABLE 2

Atomic coordinates x, y, z (×10$^4$ Å) and displacement parameters U (eq) (Å$^2$ × 10$^3$) for the example molecule 1.

| | | | | |
|---|---|---|---|---|
| C(16) | 7402.8(10) | 2049.8(9) | 5585.6(4) | 23.7(2) |
| C(21) | 8030.3(11) | 3858.2(9) | 3240.5(5) | 24.8(2) |
| C(19) | 7645.4(10) | 3096.7(8) | 4145.6(4) | 21.4(2) |
| C(22) | 8573(1) | 3936.8(9) | 2753.4(5) | 25.2(2) |
| C(1) | 6884.5(11) | 2918.2(9) | 6429.5(5) | 24.9(2) |
| C(5) | 5332.2(11) | 1756.1(9) | 5912.3(5) | 24.3(2) |
| C(40) | 7533.0(11) | 4274.0(9) | 4318.0(4) | 25.7(2) |
| N(2) | 10626.8(11) | 3462.3(12) | 1766.7(5) | 47.8(3) |
| C(25) | 9216.8(11) | 2264.9(9) | 3493.5(5) | 26.1(2) |
| C(33) | 6256.0(11) | 2827.1(10) | 3965.1(4) | 25.5(2) |
| C(30) | 8434.4(11) | 1387(1) | 5703.9(5) | 28.7(3) |
| C(32) | 8222.1(11) | 4777.5(10) | 2362.9(5) | 30.4(3) |
| C(23) | 9493.8(11) | 3196(1) | 2638.9(5) | 26.9(2) |
| C(28) | 9138.5(11) | 1837.9(9) | 4812.4(5) | 25.5(2) |
| C(29) | 9292.5(12) | 1309.6(10) | 5322.5(5) | 30.6(3) |
| C(4) | 4527.6(11) | 1832.9(9) | 6326.9(5) | 28.0(2) |
| C(6) | 4920.9(12) | 1231.6(9) | 5415.4(5) | 29.5(3) |
| C(24) | 9783.3(12) | 2364.2(10) | 3005.9(5) | 29.4(3) |
| C(39) | 6273.3(12) | 4601.8(10) | 4262.2(5) | 31.6(3) |
| C(34) | 5755.3(12) | 1848.6(11) | 3783.0(5) | 33.3(3) |
| C(2) | 6125.4(12) | 3020(1) | 6861.2(5) | 29.6(3) |
| C(3) | 4907.4(12) | 2390.2(10) | 6877.4(5) | 30.8(3) |
| C(15) | 7982.5(12) | 3530.6(10) | 6432.3(5) | 31.8(3) |
| C(7) | 3735.3(12) | 784.4(10) | 5331.2(6) | 35.6(3) |
| C(38) | 5484.3(12) | 3714.1(11) | 4032.5(5) | 32.2(3) |
| C(27) | 10145.3(12) | 1681.8(11) | 4433.3(5) | 31.4(3) |
| C(26) | 9615.5(13) | 1326.1(10) | 3858.0(5) | 31.9(3) |
| C(41) | 8492.1(14) | 4958.6(10) | 4511.5(5) | 34.9(3) |
| C(31) | 10125.5(11) | 3318.4(11) | 2151.1(5) | 32.9(3) |
| C(9) | 3345.8(12) | 1353.5(11) | 6230.5(6) | 38.1(3) |
| C(8) | 2943.3(12) | 838.5(11) | 5740.3(7) | 40.8(3) |
| C(44) | 5964.0(16) | 5627.9(11) | 4426.3(6) | 43.9(4) |
| C(11) | 5092.0(14) | 1528.7(12) | 7334.7(6) | 42.4(3) |
| C(14) | 8339.7(14) | 4229.3(11) | 6862.5(6) | 41.2(3) |
| C(10) | 3850.2(14) | 3162.4(13) | 7009.6(6) | 42.7(3) |
| C(12) | 6530.2(14) | 3722.4(12) | 7290.8(6) | 41.8(3) |
| C(35) | 4458.2(14) | 1764.8(14) | 3659.6(6) | 46.5(4) |
| C(42) | 8171.6(17) | 5992.8(11) | 4664.7(6) | 48.4(4) |
| C(37) | 4182.6(13) | 3620.1(15) | 3900.4(6) | 47.3(4) |
| C(13) | 7613.4(15) | 4322.9(13) | 7297.2(6) | 47.4(4) |
| C(43) | 6920.2(18) | 6310.2(11) | 4629.1(6) | 52.0(4) |
| C(36) | 3693.7(14) | 2642.2(17) | 3713.7(6) | 54.3(4) |

The example molecule 1 can be vacuum-sublimed (Temperature 250° C., Pressure 6×10$^{-5}$ mbar) and can also dissolve in many organic solvents, such as in Dichloromethane (CH$_2$Cl$_2$), Toluene, Tetrahydrofuran (THF), Acetone, Dimethylformamide (DMF), Acetonitrile, Ethanol, Methanol, Xylene or Benzene. The good solubility in Chloroform also allows doping, for example, in Polymethylmethacrylate (PMMA) or polystyrene.

Photophysical Measurements

Figure 5:
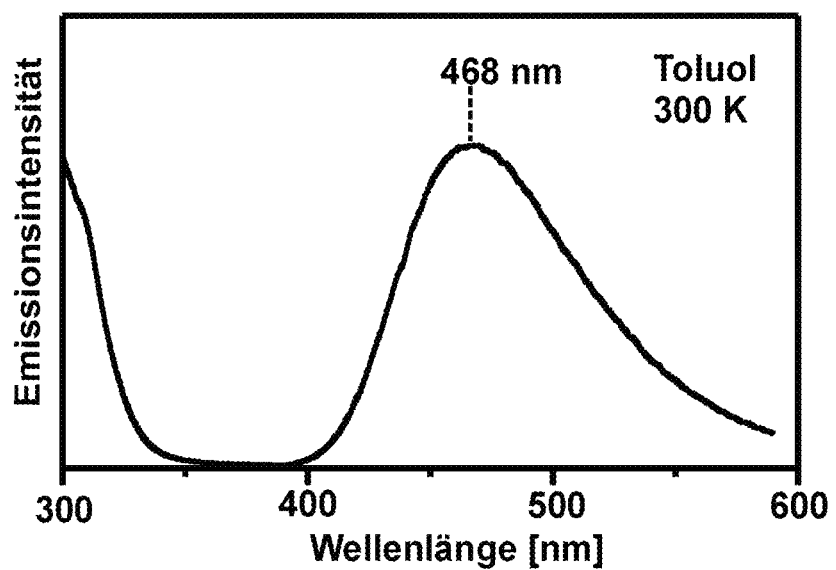
Figure 6:
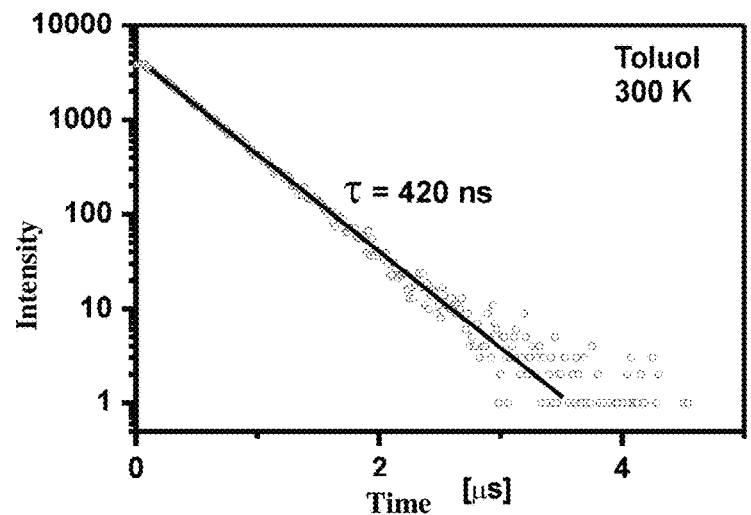

Example molecule 1 dissolved in toluene with a value of dielectric constant ε=2.4 (T=300 K) shows an emission (T=300 K) with a maximum in blue at 468 nm (FIG. 5). The emission quantum yield $\Phi_{PL}$ is high ($\Phi_{PL}$=65% for a nitrogen-purged solution). The decay time for example 1 is only 420 ns (FIG. 6). A short decay time is very important for OLED applications, because short decay time have less roll-off effects and increases the device stability, which is well-known to the person skilled in the art. Emitter has a shorter decay time, compared with the reported TADF decay time (about 5 µs).

DFT calculations (FIG. 3) show the Charge-Transfer (CT) transitions of sample molecule 1. Such transitions are influenced by the immediate vicinity of the emitter (Matrix/Solvent). FIG. 2 illustrates this behavior. With increasing polarity of the matrix, the emitting of $^1$CT-singlet state has a red shift. Corresponding statements also result from TD-DFT calculations, in which dielectric constant ε is considered mathematically as a parameter.

The effect of the polarity of the matrix is also investigated with example molecule 1 dissolved in diethyl ether. This matrix has a higher value on ε=4.3 than toluene. The emission (T=300 K) shows a red-shifted maximum at 515 nm (FIG. 7a), and the emission quantum yield $\Phi_{PL}$ is 70% in a nitrogen-purged solution. The decay time of τ=960 ns is determined (FIG. 7b). The corresponding radiative rate to kr=$\Phi_{PL}$/τ=7.3 10$^5$ s$^{-1}$ can be determined from the given values. This emission is a fluorescence equilibrated with the nearly iso-energetic $^3$CT state. Further details are given below. This interpretation is confirmed by quantum-mechanical calculations. For electronic transition S$_0$→$^1$CT, the TD-DFT calculation results (for the $^1$CT-geometry) give an oscillator strength f=0.00115. The radiative rate for the transition can be estimated based on the literature [N. Turro, Modern Molecular Photochemistry, The Benjamin/Cummings Publ., Menlo Park, Calif. 1978, page 87], using specified approximation and the energetic position of the emission (FIG. 7a). The assessment gives a radiative rate for the prompt fluorescence of kr=6.5×10$^5$ s$^{-1}$, which is relatively close to the experimentally determined rate, based on the simple approximation. The alternative interpretation, in which emission process from the triplet state is phosphorescence can be excluded for a liquid solution emitter due to the short decay time of less than 1 µs and the high emission quantum yield. This value of the decay time of 980 ns is also shorter than the shortest TADF decay time measured so far. However, the described emission process is not a TADF emission. It is, rather, fluorescence from the $^1$CT singlet state equilibrated with the nearly iso-energetic $^3$CT-state. When used in an OLED, all triplet and singlet excitons are collected. This important feature will be discussed in detail below.

Figure 8:
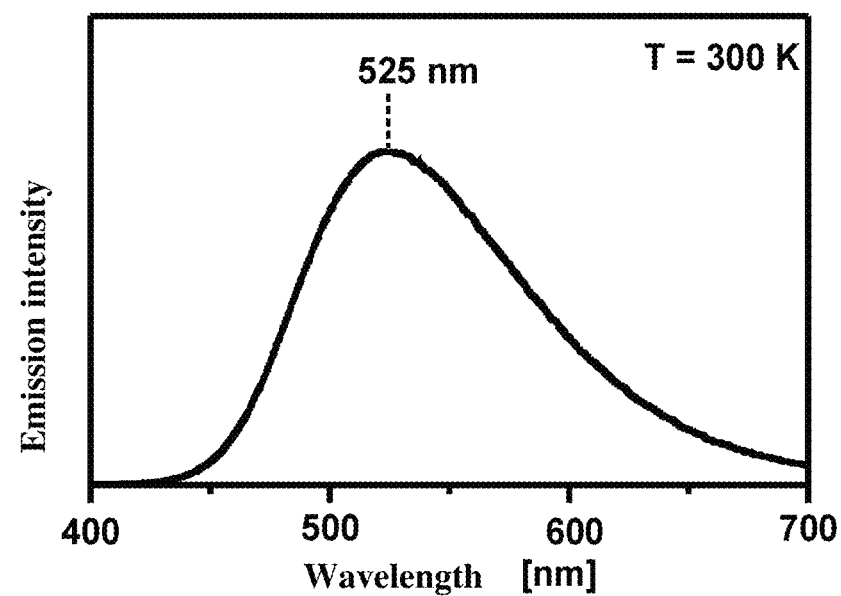

FIG. 8 shows the emission characteristics of the sample substance 1 doped in a polar matrix (with a formal ε value of ≈4.4), the higher-energy $^{1,3}$CT states of sample molecule 1 and a small singlet-triplet energy gap. This matrix is a TADF-emitter, but emission characteristics are not relevant here. The structural formula of the matrix substance is:

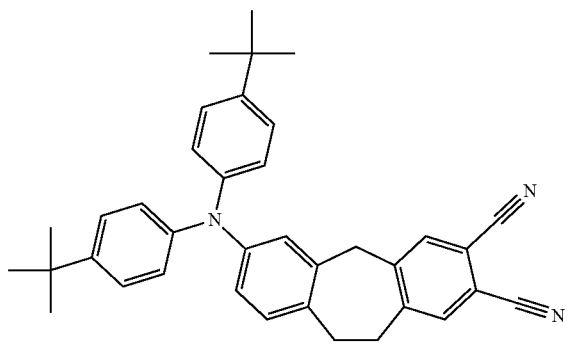 [SMILES: CC(C)(C)c1ccc(N(c2ccc(C(C)(C)C)cc2)c2ccc3c(c2)Cc2cc(C#N)c(C#N)cc2CC3)cc1]

The emission spectrum of this emitter-matrix combination/composition) is shown in FIG. 8. This emission decay time of 530 ns is also fluorescence from the $^1$CT-singlet state, which is equilibrated with the iso-energetic $^3$CT-state In FIG. 9, emission spectra of the sample molecule 1 for various temperatures (T=300 K, 150 K and 10 K) were compared. Except for a slight spectral shift, there are no changes over the entire temperature range, as expected, in contrast to TADF-emitter (freezing of TADF emissions). The radiative rate of emission does not change significantly either. These measurement results show that the emission mechanism remains unchanged over the entire temperature range, expected as fluorescence from the 1CT-singlet state equilibrated with iso-energetic $^3$CT-state.

Figure 10:
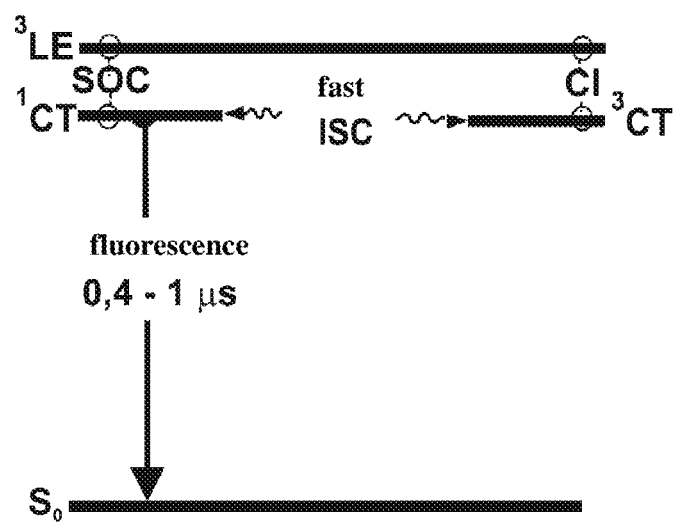

In FIG. 10, the emission behavior of the sample molecule 1 in a polar environment such as diethyl ether or the discussed solid TADF matrix, is displayed with an energy level diagram. Low temperature measurements show that the localized $^3$LE-state energy is above the $^{1,3}$CT states.

Quantum mechanical mixtures of this $^3$LE state via the mechanisms of SOC (spin-orbit coupling=spin-orbit interaction) and the configuration interaction (CI) are possible with the CT-states. Furthermore, since the singlet and triplet CT states have similar potential areas, the Franck-Condon factors responsible for the ISC rate are large. (This term is known to a person skilled in the art) Because of these properties, it is expected that rapid ISC occurs between the $^1$CT state and the $^3$CT state. "Fast" means that the ISC processes take place faster than the prompt fluorescence in this context. In fact, even at low temperature (e.g. T=10 K), no $^3$CT phosphorescence was observed for molecule 1 in the TADF matrix.

When the composition (emitter molecules in a polar matrix) is used in an OLED, the singlet excitons occupy the CT-singlet and triplet excitons occupy the CT-triplet state according to the invention. Since the occupation of both CT states is in equilibrium with the rapid ISC processes and the prompt $^1$CT→S$_0$ fluorescence is much faster than the spin-forbidden $^3$CT→S$_0$ phosphorescence, fluorescence from the $^1$CT-singlet states equilibrated with the nearly iso-energetic $^3$CT state can be observed. This means that all excitation processes can lead to the direct occupation and emission from the CT singlet state. That is, there is a "direct singlet harvesting". This invention thus provides organic emitter molecules for optoelectronic devices, as well as a method for adapting these, which lead to a significant shortening of the emission decay time (eg., by a factor of five to ten) compared to the prior art.

Example 2

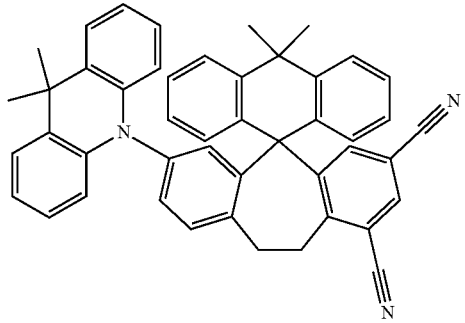 [SMILES: CC1(C)c2ccccc2N(c2ccc3c(c2)C2(c4ccccc4C(C)(C)c4ccccc42)c2cc(C#N)cc(C#N)c2CC3)c2ccccc21]

Example Molecule 2

Figure 11:
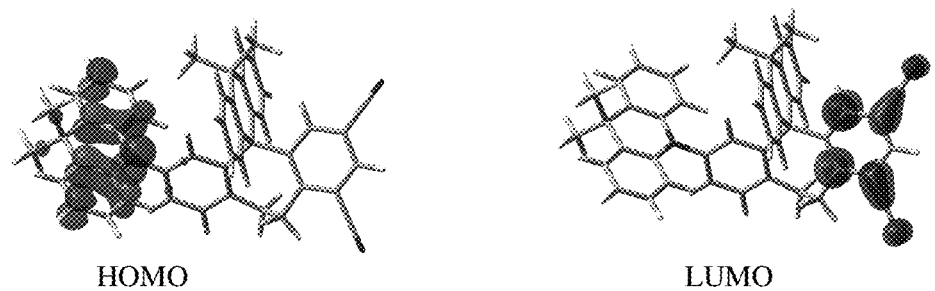

The frontier orbitals shown in FIG. 11 indicate that HOMO and LUMO are located in distinctly different spatial regions of the molecule. This suggests a very small splitting between the lowest triplet CT and the above singlet CT state. A calculation for the sample molecule 2 in a TD-DFT calculation (Functional B3LYP; basic set 6-31G (d, p)) shows that this energy difference for the optimized singlet geometry ΔE ($^1$CT-$^3$CT)=5 cm$^{-1}$ is (0.6 meV). Thus, example molecule 2 represents an organic molecule of the invention.

The chemical synthesis of the molecule Example 2 started from commercially available starting materials is explained in the following scheme.

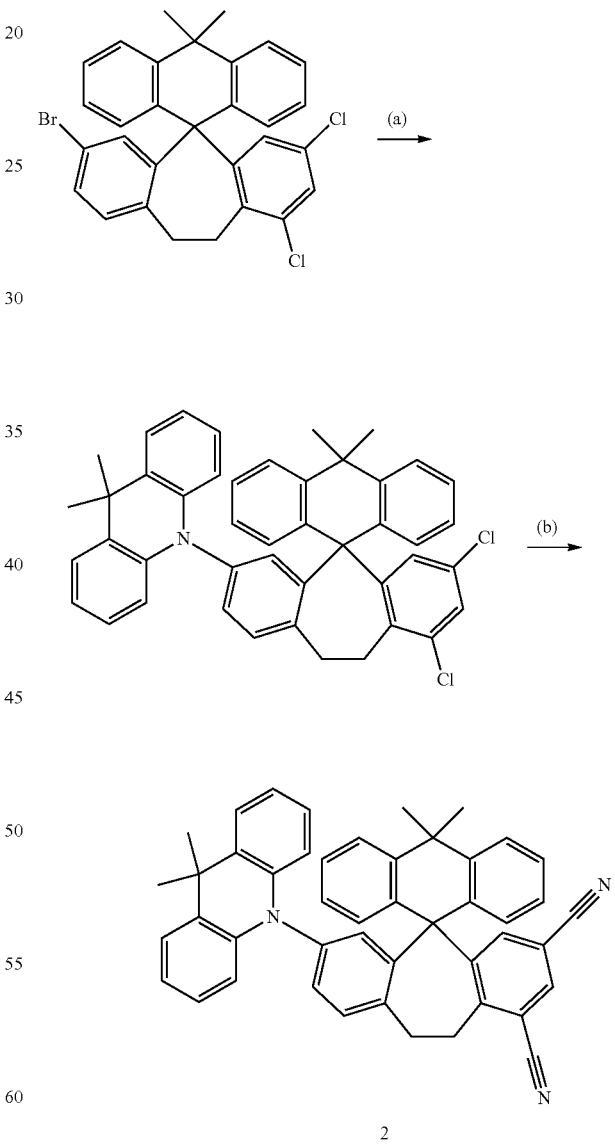

2

Reactants and reaction conditions: (a) 9,9-dimethyl-9,10-dihydroacridin, Pd(CH$_3$COO)$_2$, P[(C(CH$_3$)$_3$]$_3$, (CH$_3$)$_3$CONa, 90° C., 19 h. (b) Zn(CN)$_2$, 1,1'-bis (diphenylphosphino) ferrocene, [1,1'-bis (diphenylphosphino)ferrocene] dichloropalladium (II) complex with dichloromethane, N-methyl-2-pyrrolidone, 180° C., 12 h.

Example 3

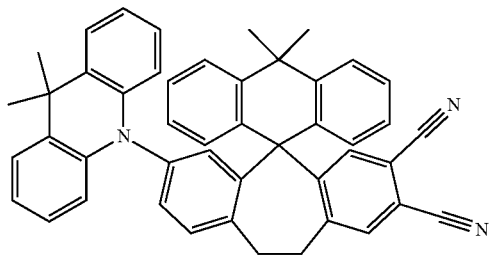 [SMILES: CC1(C)c2ccccc2N(c2ccc3c(c2)C2(c4cc(C#N)c(C#N)cc4CC3)c3ccccc3C(C)(C)c3ccccc32)c2ccccc21]

Example Molecule 3

Figure 12:
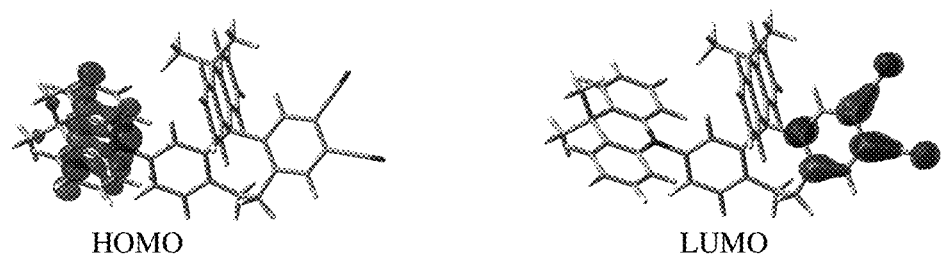

The frontier orbitals shown in FIG. 12 indicate that HOMO and LUMO are located in distinctly different spatial regions of the molecule. This suggests that the splitting between the lowest triplet CT and the above singlet CT state is small. Calculation for the sample molecule 3 in a TD-DFT calculation (Functional B3LYP; basic set 6-31G (d, p)) shows that the energy gap $\Delta E$ ($^1CT$-$^3CT$) for the optimized singlet geometry is 5 cm$^{-1}$ (0.6 meV). Thus, example molecule 3 represents an organic molecule of the invention.

The chemical synthesis of the molecule example 3 started from commercially available starting materials is explained in the following Scheme.

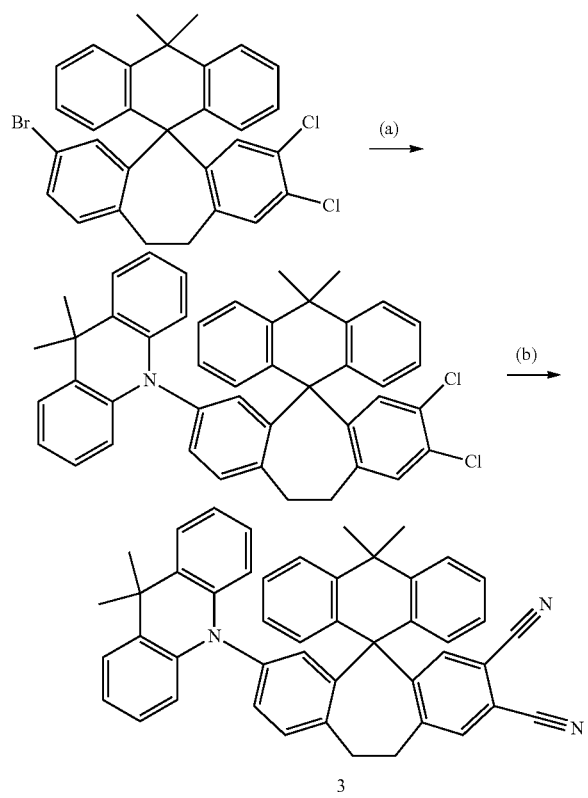

3

Reactants and reaction conditions: (a) 9,9-dimethyl-9,10-dihydroacridin, Pd(CH$_3$COO)$_2$, P[(C(CH$_3$)$_3$]$_3$, (CH$_3$)$_3$CONa, 90° C., 19 h. (b) Zn(CN)$_2$, 1,1'-bis (diphenylphosphino) ferrocene, [1,1'-bis (diphenylphosphino)ferrocene] dichloropalladium (II) complex with dichloromethane, N-methyl-2-pyrrolidone, 180° C., 12 h.

Example 4

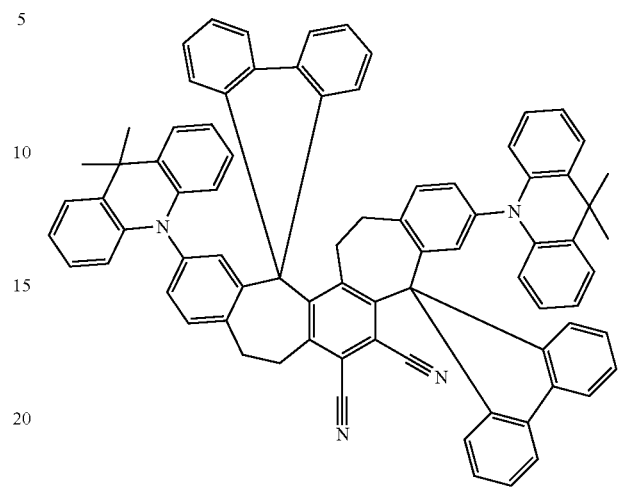

Example Molecule 4

Calculation for the sample molecule 4 in a TD-DFT calculation (Functional B3LYP; basic set, 6-31G (d, p)) shows that the energy gap $\Delta E$ ($^1CT$-$^3CT$) for the optimized triplet geometry is 8 cm$^{-1}$ (1 meV). Thus, example molecule 4 represents an organic molecule of the invention.

The chemical synthesis of the example molecule 4 started from commercially available starting materials is explained in the following Scheme.

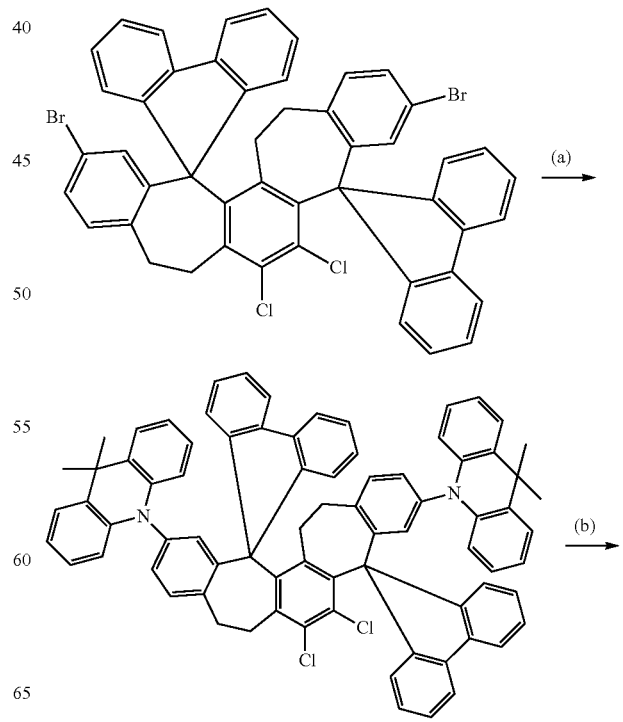

-continued

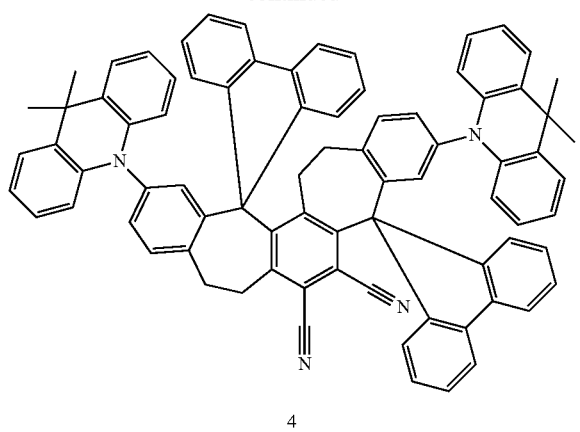

4

Reactants and reaction conditions: (a) 9,9-dimethyl-9,10-dihydroacridin, Pd(CH₃COO)₂, P[(C(CH₃)₃]₃, (CH₃)₃CONa, 90° C., 19 h. (b) Zn(CN)₂, 1,1'-bis (diphenylphosphino)ferrocene, [1,1'-bis (diphenylphosphino)ferrocene] dichloropalladium (II) complex with dichloromethane, N-methyl-2-pyrrolidone, 180° C., 12 h.

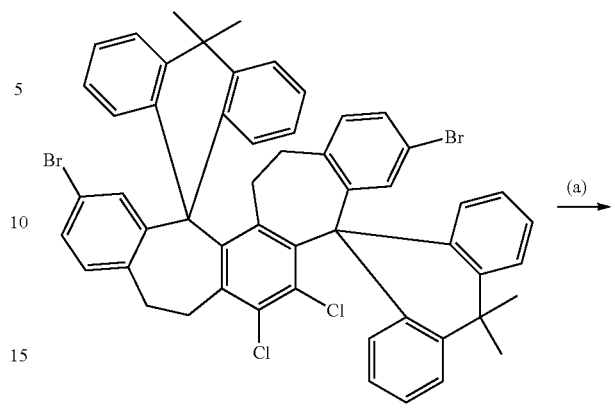

Example 5

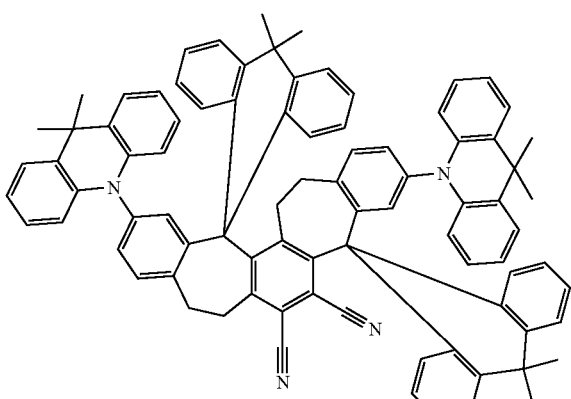

Example Molecule 5

Calculation for the sample molecule 5 in a TD-DFT calculation (Functional B3LYP; basic set 6-31G (d, p)) shows that the energy gap $\Delta E$ ($^1CT$-$^3CT$) for the optimized triplet geometry is 9 cm$^{-1}$ (1.1 meV). Thus, example molecule 5 represents an organic molecule of the invention.

The chemical synthesis of the molecule example 5 started from commercially available starting materials is explained in the following Scheme.

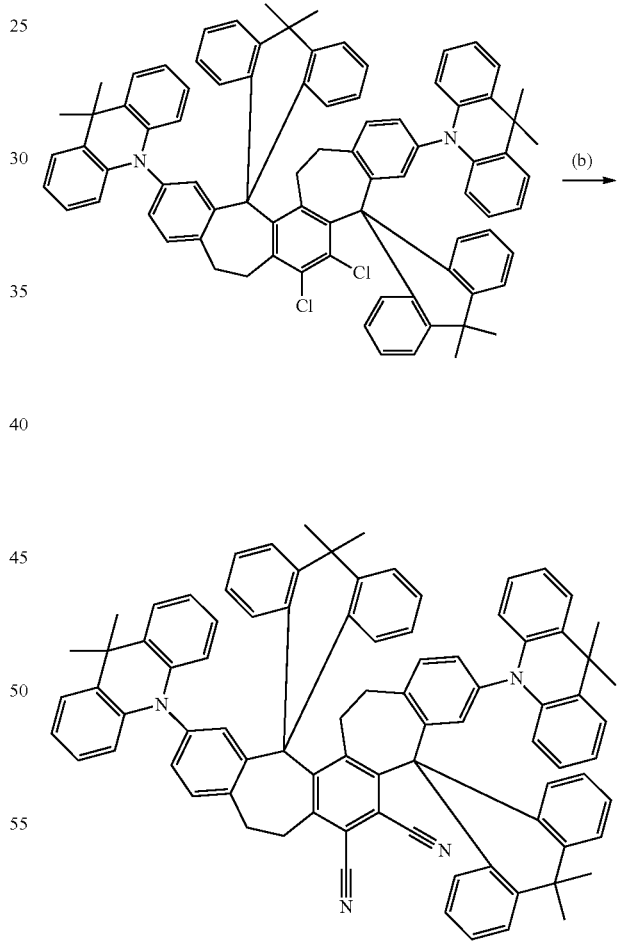

5

Reactants and reaction conditions: (a) 9,9-dimethyl-9,10-dihydroacridin, Pd(CH₃COO)₂, P[(C(CH₃)₃]₃, (CH₃)₃CONa, 90° C., 19 h. (b) Zn(CN)₂, 1,1'-bis(diphenylphosphino)ferrocene, [1,1'-bis(diphenylphosphino)ferrocene]dichloropalladium (II) complex with dichloromethane, N-methyl-2-pyrrolidone, 180° C., 12 h.

Example 6

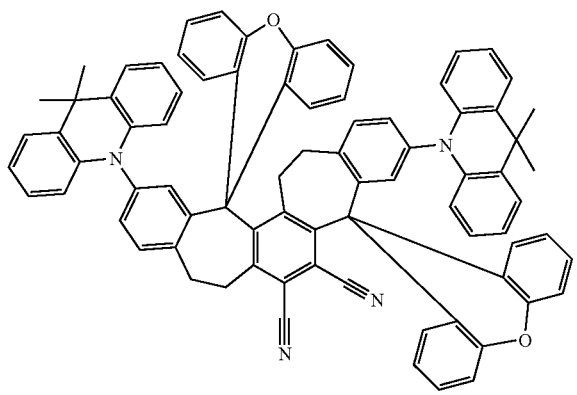 [SMILES: CC1(C)c2ccccc2N(c2ccc3c(c2)C2(c4ccccc4Oc4ccccc42)c2c(C#N)c(C#N)c4c(c2CC3)C2(c3cc(N5c6ccccc6C(C)(C)c6ccccc65)ccc3CC4)c3ccccc3Oc3ccccc32)c2ccccc21]

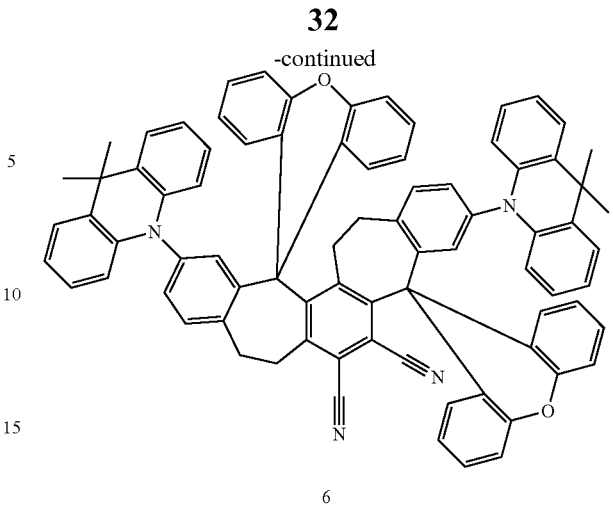

Reactants and reaction conditions: (a) 9,9-dimethyl-9,10-dihydroacridin, Pd(CH₃COO)₂, P[(C(CH₃)₃]₃, (CH₃)₃CONa, 90° C., 19 h. (b) Zn(CN)₂, 1,1'-bis(diphenylphosphino) ferrocene, [1,1'-bis(diphenylphosphino)ferrocene]dichloropalladium(II) complex with dichloromethane, N-methyl-2-pyrrolidone, 180° C., 12 h.

Example Molecule 6

Calculation for the sample molecule 6 in a TD-DFT calculation (Functional B3LYP; basic set, (6-31G (d, p)) shows that the energy gap $\Delta E$ ($^1$CT-$^3$CT) for the optimized triplet geometry is 12 cm$^{-1}$ (1.5 meV). Thus, example molecule 6 represents an organic molecule according to the invention.

The chemical synthesis of the molecule example 6 started from commercially available starting materials is explained in the following scheme.

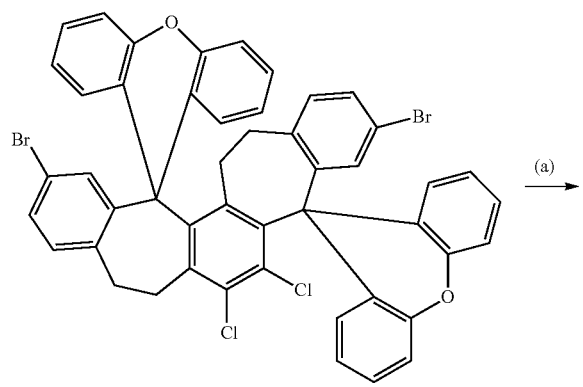

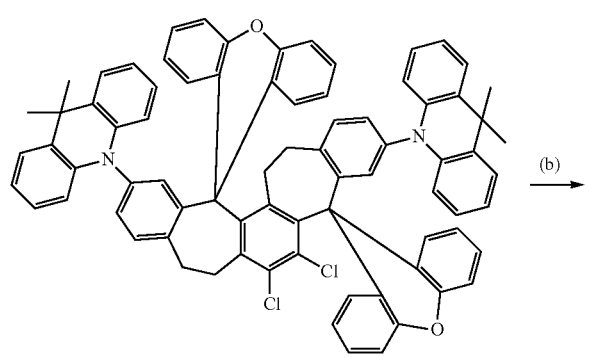

Figure 13:
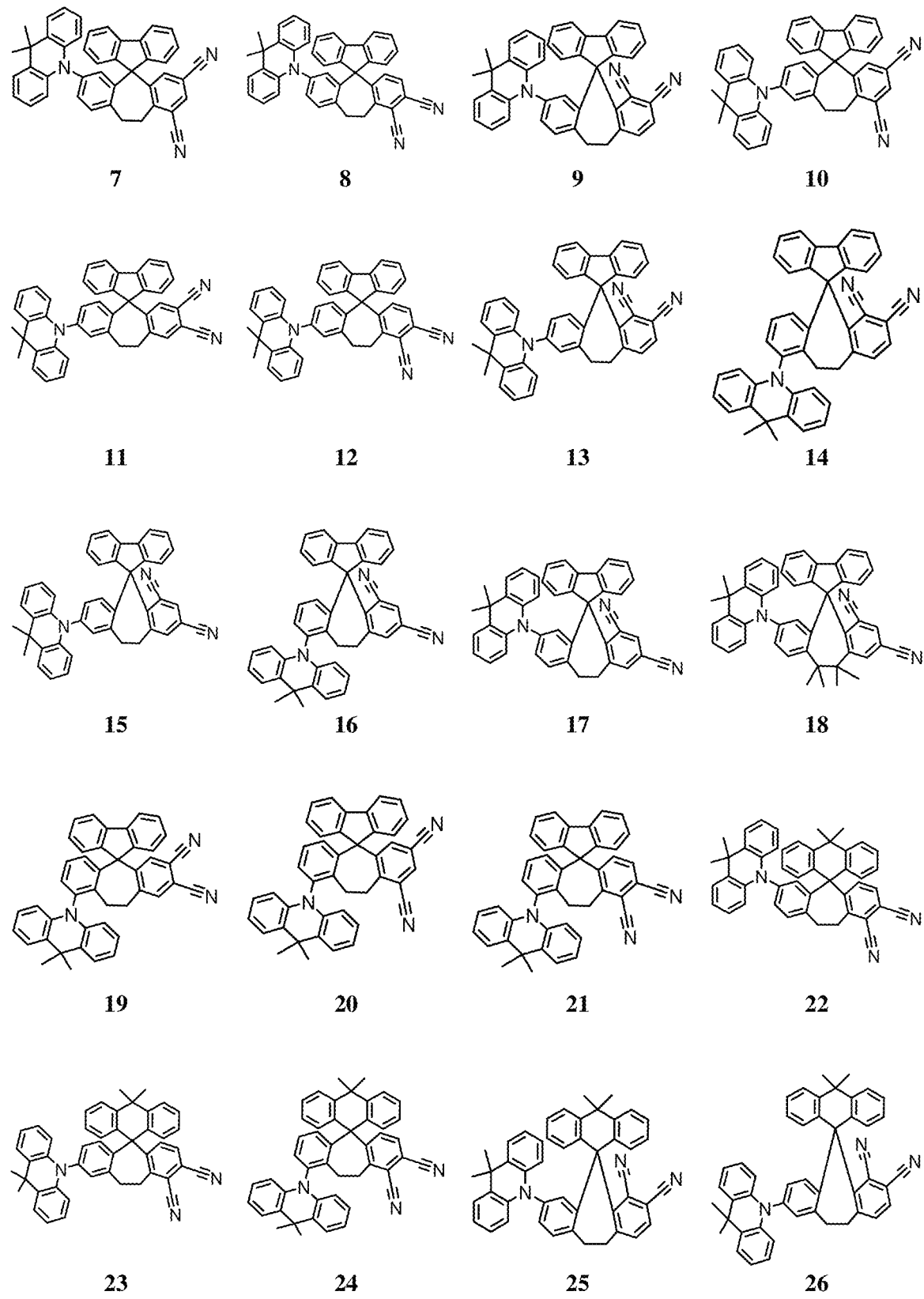

FIG. 13 shows another example molecule of the invention.

FIGURE

FIG. 1: Energy level diagram illustrates the process of thermally activated delayed (delayed) fluorescence (TADF). $k_B$ represents the thermal energy $k_B$ of the Boltzmann constant and T is the absolute temperature. The diagram shows the radiative TADF process, observed at low temperature and non-radiating (wavy) deactivation from the $T_1$ state. The process of spontaneous $S_1 \rightarrow S_0$ fluorescence is not shown in the diagram.

Figure 2:
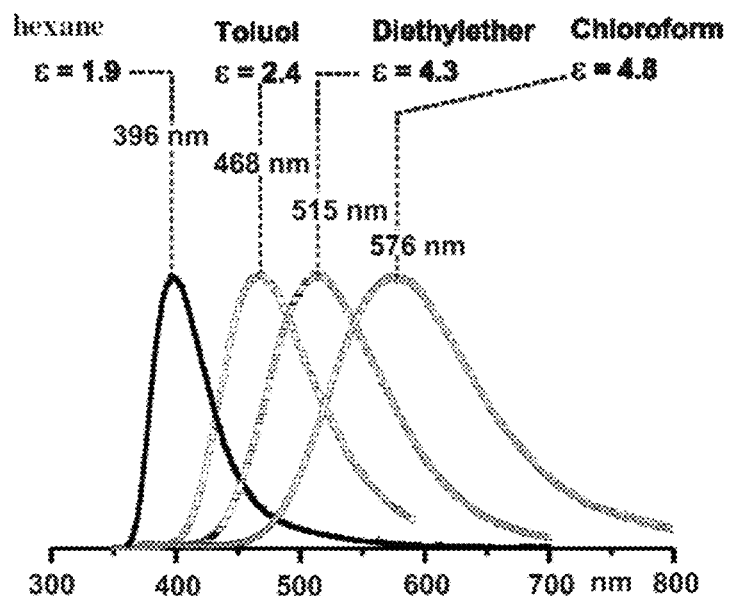

FIG. 2: Influence of polarity of the solvent on the energy position of the $^1$CT-emission for the dissolved sample molecule 1 at T=300 K. The figure shows the red shift of the emission spectra with increasing polarity of the solvent (quantified by the dielectric constant ε).

FIG. 3: Isosurfaces of the frontier orbitals for the sample molecule 1 (see example 1), HOMO: left, LUMO: right. Geometry optimizations were carried out for the electronic ground state $S_0$. Calculation methods: DFT and TD-DFT, Functional: B3LYP, basic set: 6-31G (d, p), calculation software: Gaussian 09. The calculations show the energy gap between the singlet CT state and the triplet-CT state is 7 cm$^{-1}$ ($T_1$ geometry). This value indicates that example 1 is a good emitter for use in optoelectronic devices.

FIG. 4: Perspective view of example molecule 1, resulted from an X-ray structure determination. The single crystal used for structure analysis was performed by slow diffusion of hexane into a saturated dichloromethane solution of 1.

FIG. 5: Emission and excitation spectrum of example substance 1 dissolved in toluene (c≈10$^{-5}$ M). The residual oxygen was removed from the solution by passing nitrogen over 120 minutes. The emission quantum yield was $\Phi_{PL}$=65%. Excitation: 310 nm, detection: 468 nm.

FIG. 6: TADF decay time of the sample molecule 1 dissolved in toluene and nitrogen-purged (T=300K, c≈10$^{-5}$ M). Excitation: 310 nm, pulse duration: 10 ns. The measured value of τ=420 ns represents the shortest decay time, which is significantly shorter than the previously measured TADF shortest decay time.

Figure 7:
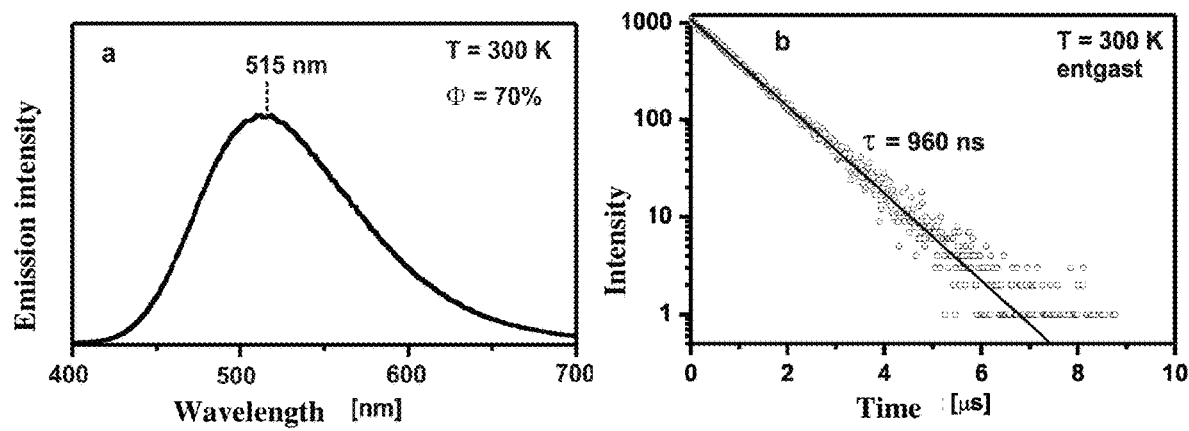

FIG. 7: (a) Emission spectrum of example molecule 1 in diethyl ether (c≈10$^{-5}$ M). The emission represents the $^1$CT-fluorescence equilibrated with the $^3$CT state with a decay time of τ=960 ns (b). The sample was purged with nitrogen for 120 minutes. Excitation: Spectrum (a): 310 nm (cw-LED); Decay curve (b): 310 nm (LED pulsed). Temperature (T)=300 K.

FIG. 8: Emission spectrum of example molecule 1 in a fixed TADF matrix (see text) (c≈10 wt. %). The emission represented a fluorescence equilibrated with $^3$CT-state with a decay time of 530 ns. The sample was carefully degassed. Excitation: 310 nm (cw-LED). Temperature (T)=300 K.

Figure 9:
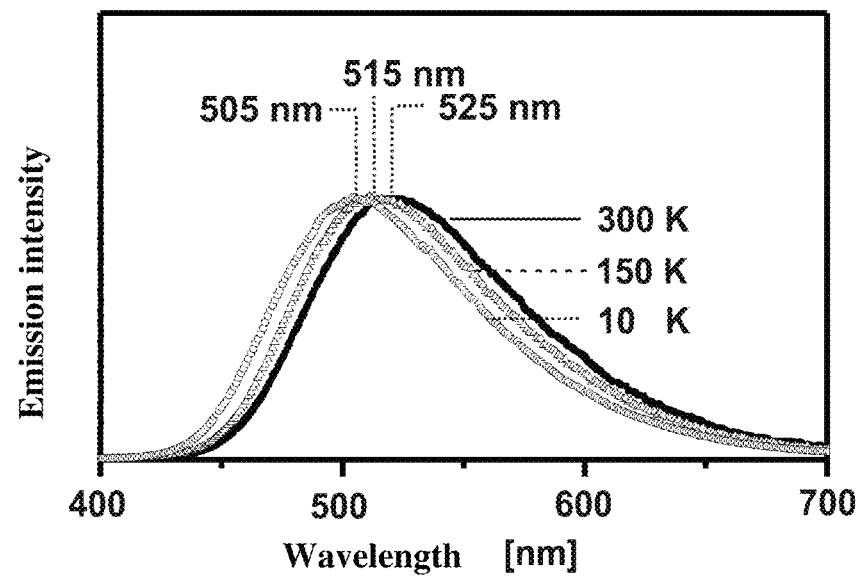

FIG. 9: Emission spectra of example molecule 1 in a fixed TADF matrix (see text) (c≈10 wt. %) at various temperatures (spectra normalized). The emission spectra vary only slightly with cooling. The decay times are extended from 530 ns (300 K) to ≈1 us (10 K). The radiative rate changes only slightly with cooling.

FIG. 10: Energy level diagram for explaining the emission behavior of the example molecule 1 in a polar matrix, such as diethyl ether or the above-described TADF matrix. The localized $^3$LE state is energetically above the $^{1,3}$CT states. The states can comprise quantum mechanical mixtures, namely the $^3$LE-state and the $^1$CT-state can be mixed by spin-orbit coupling (SOC), while the two triplet states can interact through configuration interaction (CI). This result is in a rapid intersystem crossing (ISC) between the $^1$CT and the $^3$CT state. As a result, even at low temperature, only $^1$CT-fluorescence equilibrated with the $^3$CT state can be observed, neither a $^3$CT phosphorescence, nor a TADF.

FIG. 11: Isosurfaces of the frontier orbitals for the sample molecule 2 (see example 2.), HOMO: left, LUMO: right. Geometry optimizations were carried out for the electronic ground state $S_0$. Calculation methods: DFT and TD-DFT, Functional: B3LYP, basic rate: 6-31G (d, p), Calculation software: Gaussian 09. The calculations predict 5 cm$^{-1}$ (0.6 meV) ($S_0$ geometry) for the energy difference between the singlet CT state and the triplet-CT state.

FIG. 12: Isosurfaces of the frontier orbitals for the sample molecule 3 (see example 3.), HOMO: left, LUMO: right. It made geometry optimizations for the electronic ground state $S_0$. Accounting methods: DFT and TD-DFT, Functional: B3LYP, basic rate: 6-31G (d, p), invoice Software: Gaussian 09. The calculations predict for the energy gap between the singlet state and the triplet CT-CT state 5 cm$^{-1}$ ($S_0$ (0.6 MeV) geometry).

FIG. 13: Further examples of the invention organic emitter molecules that are suitable for the usage in opto-electronic devices.

The invention claimed is:

1. An optoelectronic device, comprising:
   an active component in which, upon excitation of an organic molecule, there are direct and fast relaxation and intersystem crossing processes for filling the charge transfer singlet state ($^1$CT) from the substantially isoenergetic charge transfer triplet state ($^3$CT) of the organic molecule, so that a $^1$CT→$S_0$ fluorescence occurs, without the need for thermal activation, where $S_0$ stands for the electronic ground state, wherein:
   the organic molecule has a structure of formula Ia or Ib, or of a structure according to formula Ia or Ib:

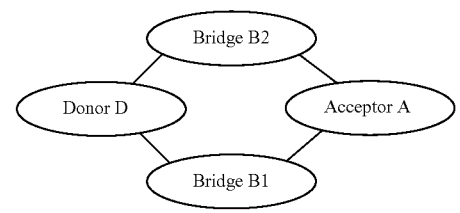

Formula Ia

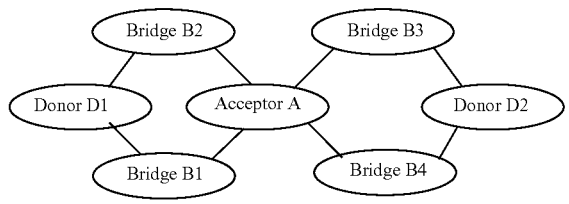

Formula Ib the organic molecule includes:
   an aromatic or hetero-aromatic donor member Donor D or aromatic or hetero-aromatic donor members Donor D1 and Donor D2, wherein each donor member is substituted with electron-donating or -withdrawing substituents, and
   two or four non-conjugated bridge members selected from Bridge B1, Bridge B2, Bridge B3 and Bridge B4 bound to aromatic or hetero-aromatic acceptor segment Acceptor A that is substituted with electron-donating or -withdrawing substituents, and
the bridge members Bridge B1, Bridge B2, Bridge B3, Bridge B4 are chosen such that there is a prevention of overlap between a HOMO of the donor segment and a LUMO of the acceptor segment.

2. An optoelectronic device of claim 1, wherein a direct rapid occupation of the charge transfer singlet state $^1$CT, compared to molecules which show thermally activated delayed fluorescence (TADF), in addition, results in 5 to 10 time faster emission decay from this charge transfer singlet state $^1$CT.

3. An optoelectronic device of claim 1, wherein an emission decay time of the organic molecule is less than 2 microseconds.

4. An opto-electronic device of claim 1, wherein an emission of the $^1$CT→$S_0$ fluorescence is not a TADF emission.

5. An optoelectronic device of claim 1, wherein the $^1$CT→$S_0$ fluorescence with a substantially isoenergetic charge transfer triplet ($^3$CT) equilibrated state fluorescence from the $^1$CT is singlet.

6. Opto-electronic device of claim 1, wherein the organic molecule has a structure to one of the following displayed formulas or consists of such a structure:

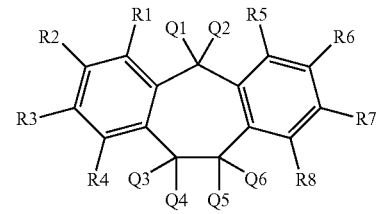

Formel IIa

-continued

Formel IIb

Formel IIc

Formel IId

Formel IIe wherein:
the 2,3: 6,7-dibenzosuberane backbone is substituted so the electronic properties of the aromatic ring systems are modified,
the bridge members include:
Q1, Q2, and Q1' Q2' are independently selected from the group consisting of alkyl, alkenyl, alkynyl, cycloalkyl and aryl; and
Q3 to Q6 and Q3' to Q6' are independently selected from the group consisting of H, alkyl, alkenyl, alkynyl, cycloalkyl and aryl;

wherein:
Alkyl is a straight-chain (unbranched) or branched ($C_1$-$C_{10}$) alkyl having 1 to 10 carbon atoms in the main hydrocarbon chain,
Alkenyl is a straight or branched ($C_1$-$C_{10}$) alkenyl having 1 to 10 carbon atoms in the main hydrocarbon chain,
Alkynyl is a straight or branched ($C_1$-$C_{10}$) alkynyl, having 1 to 10 carbon atoms in the main hydrocarbon chain,
Cycloalkyl is a ($C_3$-$C_7$) -cycloalkyl having 3 to 7 ring carbon atoms, and
Aryl is a 5-membered ring or 6-membered ring aromatic or heteroaromatic group,
"main hydrocarbon chain" used herein is the longest chain of the branched or non-linear alkyl, alkenyl or alkynyl;
wherein:
each group Q1 to Q6 and Q1' to Q6' independently may be substituted or unsubstituted with one or more F, Cl, Br, alkoxyl, thioalkoxyl, amine, silane, phosphine, borane, or aryl;
the groups Q1 and Q2, Q3 and Q4 groups, the groups Q5 and Q6, the groups Q1' and Q2', the groups Q3' and Q4', as well as the groups Q5' Q6' and are optionally chemically linked together to form other ring systems;
the donor members include:
R1 to R4 and R1' to R4' are independently selected from the group consisting of H, alkyl, alkenyl, alkynyl, cycloalkyl, alkoxyl, thioalkoxyl, amine, phosphine, silane, borane, fluorine, chlorine, bromine, or an Akr group defined by Formula IIIa or Formula IIIb,
in Formula IIa, at least one of R1 to R4 is independently the Akr group;
in Formulae IIb to IIe at least one of R1 to R4 is independently the Akr group and at least one of R1' to R4' is independently the Akr group,
wherein:
Alkyl is a straight or branched ($C_1$-$C_{10}$) alkyl having 1 to 10 carbon atoms in the main hydrocarbon chain,
Alkenyl is a straight or branched ($C_1$-$C_{10}$) alkenyl having 1 to 10 carbon atoms in the main hydrocarbon chain,
Alkynyl is a straight or branched ($C_1$-$C_{10}$) alkynyl, having 1 to 10 carbon atoms in the main hydrocarbon chain,
Cycloalkyl is a ($C_3$-$C_7$) -cycloalkyl having 3 to 7 ring carbon atoms, and
Aryl is a 5-membered ring or 6-membered ring aromatic or heteroaromatic group,
wherein the alkoxyl, thioalkoxyl, amine, phosphine, silane and borane is in each case an alkoxyl OR', SR' thioalkoxyl, amine NR'R", phosphine PR'R", silane SiR'R"R'" and borane BR'R" wherein R', R" and R'" is independently a straight or branched ($C_1$-$C_{10}$) alkyl, ($C_1$-$C_{10}$)-alkene, ($C_1$-$C_{10}$) alkyne, ($C_3$-$C_7$) cycloalkyl or a 5-membered ring or 6-membered ring aromatic or heteroaromatic group;

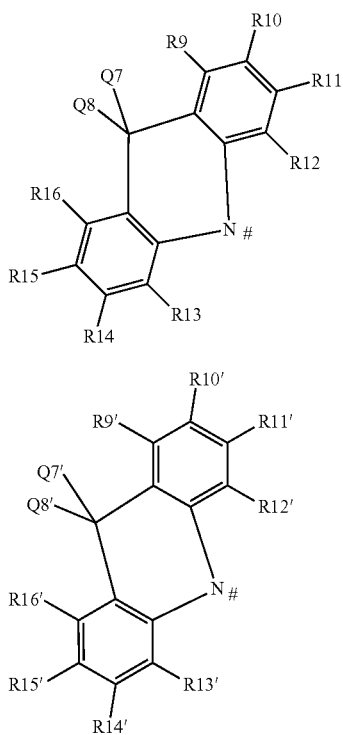

Formula IIIa

Formula IIIb wherein:

\# marks the point through which the Akr group is connected to the rest of the molecule, R9 to R16 and R9' to R16' are independently selected from H, $(C_1\text{-}C_{10})$ alkyl, $(C_1\text{-}C_{10})$-alkenyl, $(C_1\text{-}C_{10})$-alkynyl, $(C_3\text{-}C_7)$ cycloalkyl, alkoxyl OR', amine NR'R", phosphine PR'R", silane SiR'R"R''', borane BR'R", fluorine, chlorine, bromine, or aryl, wherein the R', R" and R''' is a straight or branched $(C_1\text{-}C_{10})$ alkyl, $(C_1\text{-}C_{10})$ alkene, $(C_1\text{-}C_{10})$ alkyne, $(C_3\text{-}C_7)$ cycloalkyl or a 5 membered ring or 6-membered ring aromatic or heteroaromatic group;

Q7, Q8, and Q7' Q8' are defined as Q1 to Q6 and Q1' to Q6' and may be linked together to form a further ring system;

the acceptor segment includes:

R5 to R8 are independently selected from H, $CH_3$, CN, COR', CO (OR'), CO (NR'R"), $SO_2R'$, $SO_2$ (OR'), SOR', $CF_3$, $CF_2R'$, wherein R' and R" are straight or branched $(C_1\text{-}C_{10})$ alkyl, $(C_1\text{-}C_{10})$ alkene, $(C_1\text{-}C_{10})$ alkyne, $(C_3\text{-}C_7)$ cycloalkyl or a 5-membered ring or 6-membered ring aromatic or heteroaromatic group, and at least one group is not H or $CH_3$;

wherein in the formula IIa, at least two substituents selected from R5, R6, R7 and R8 are not H or $CH_3$.

7. An opto-electronic device of claim 6, wherein the organic molecule has or consists of a structure according to the formulas IVa to IVd:

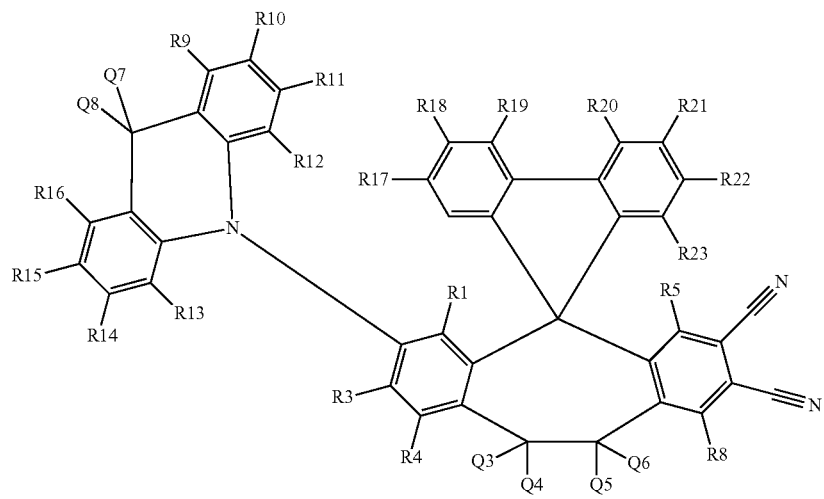

Formula IVa

-continued
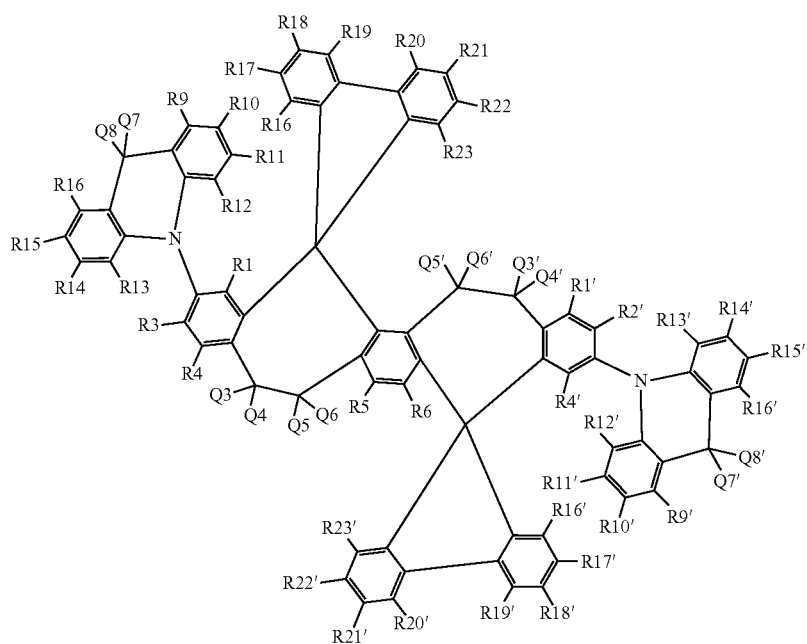
Formula IVb
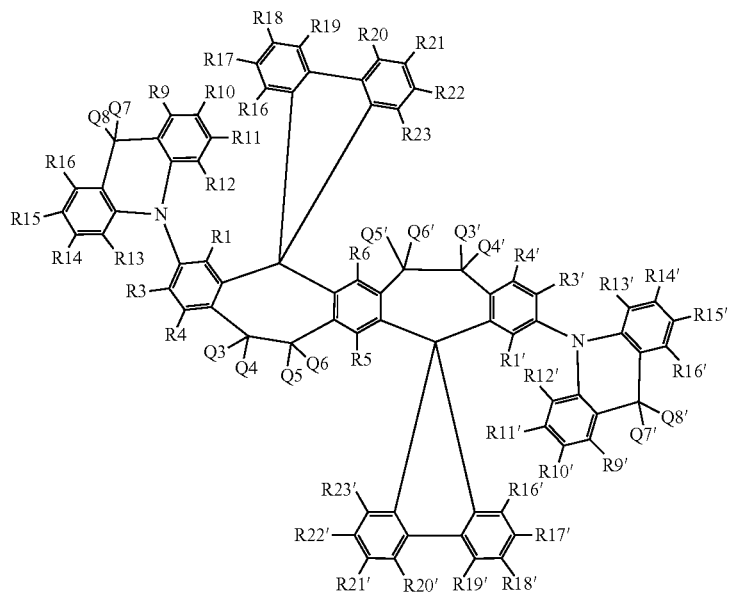
Formula IVc

-continued

Formula IVd

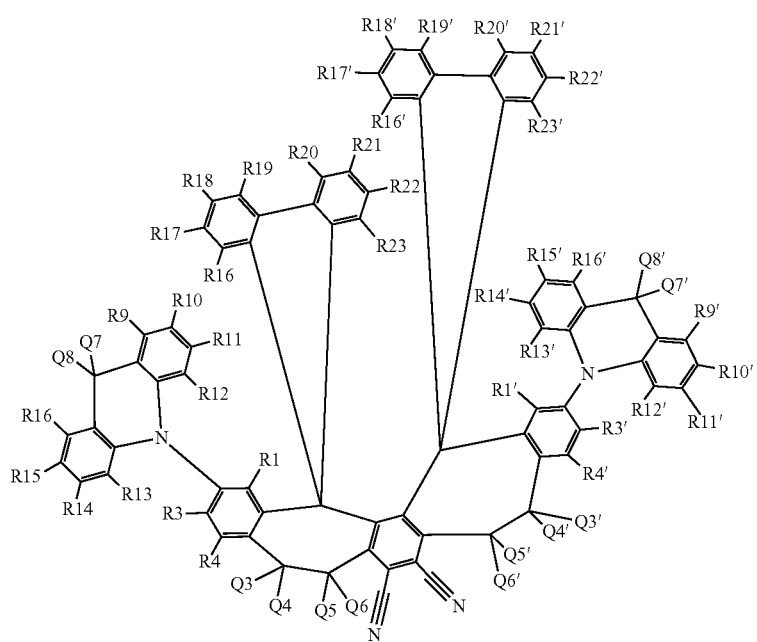

wherein R17 to R23 and R17' to R23' are defined as R9 to R16 and R9' to R16'.

8. An opto-electronic device of claim 6, wherein the organic molecule has or consists of a structure according to formula V;

Formel V

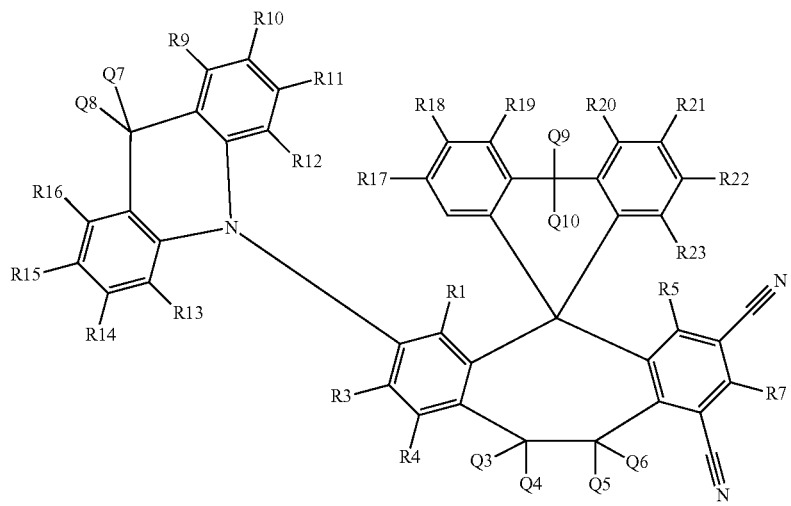

wherein:
R17 to R23 are defined as R9 to R16, and
Q9 and Q10 are defined as Q1 to Q8 and Q1' to Q8' and are optionally linked to one another so that a further ring system is formed.

9. An optoelectronic device of claim 6, wherein the organic molecule has or consists of a structure according to formula VI:

Formel VI
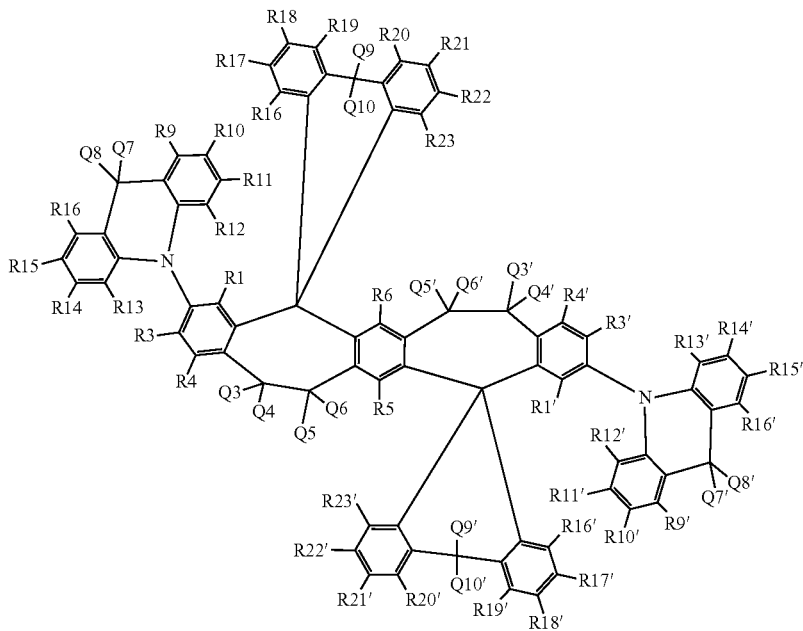
R17 to R23 and R17' to R23' are defined as R9 to R16, Q9' and Q10' are defined as Q1' to Q8' and are optionally linked to one another to further form a ring system.
10. An optoelectronic device of claim 6, wherein the organic molecule has or consists of a structure according to the formulas VII to XVI:
Formula VII
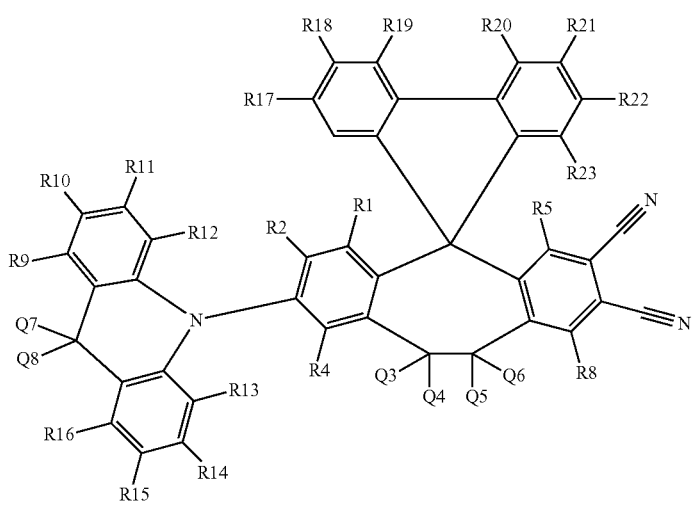

Formula VIII
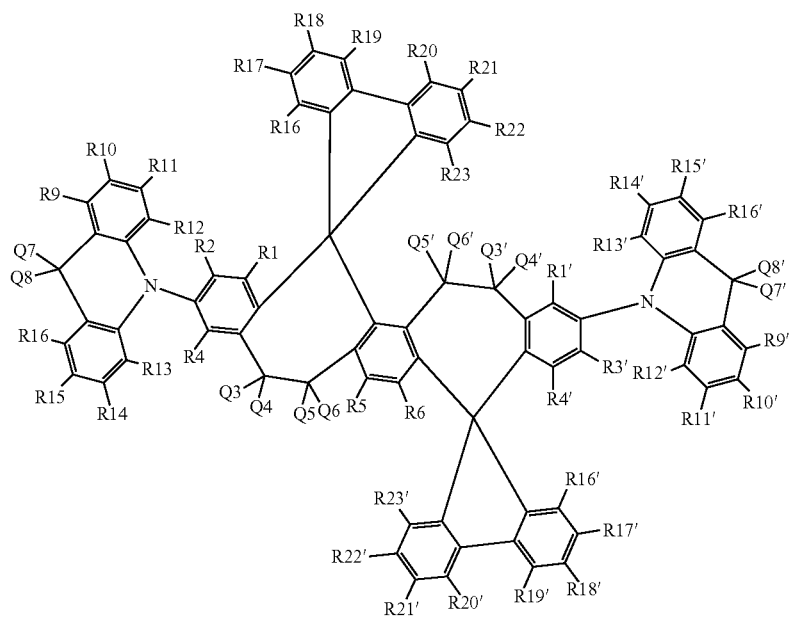
Formula IX
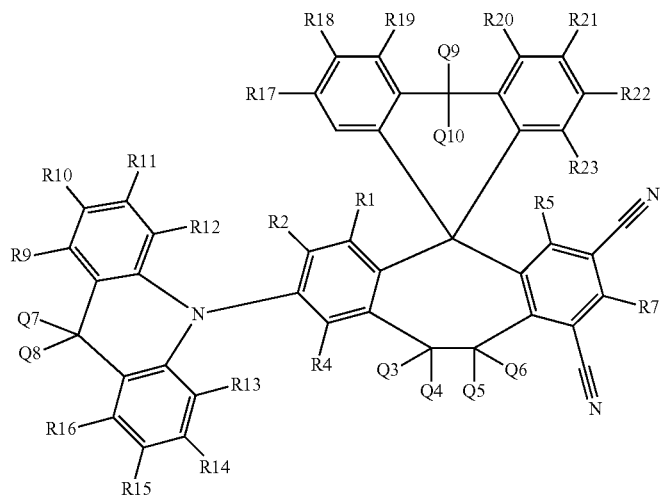

-continued
Formula X
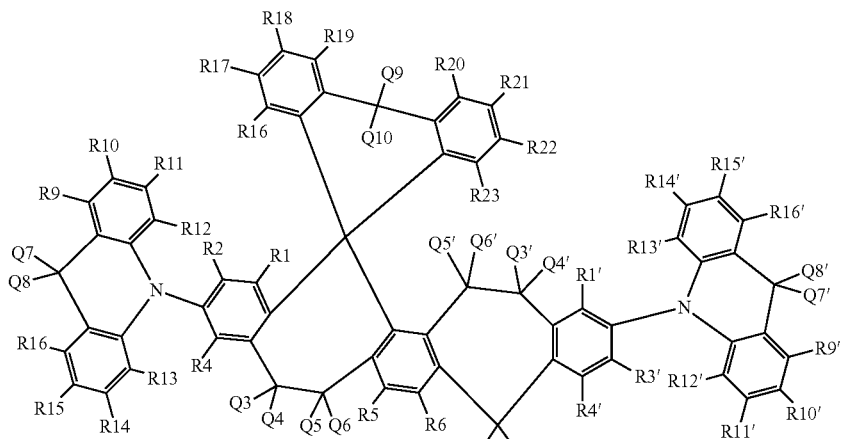
Formula XI
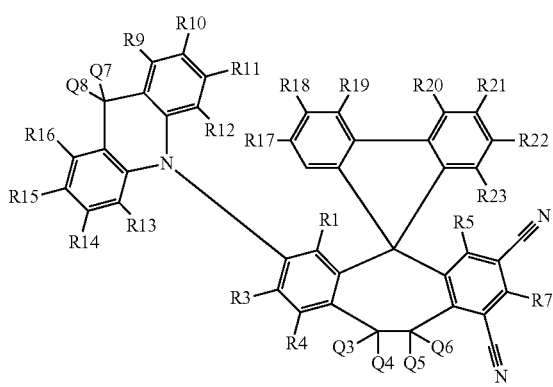
Formula XII
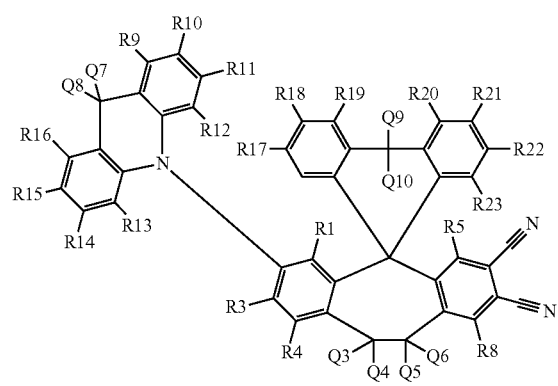
Formula XIII
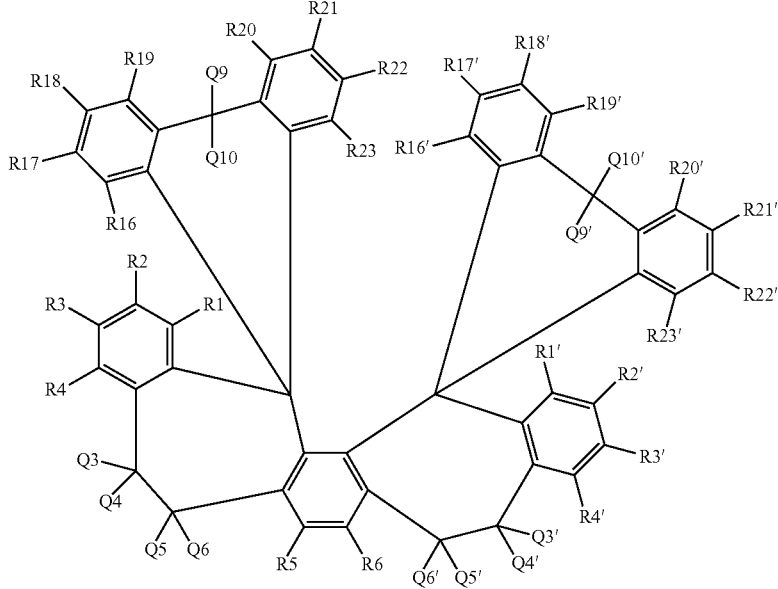

-continued

Formula XIV

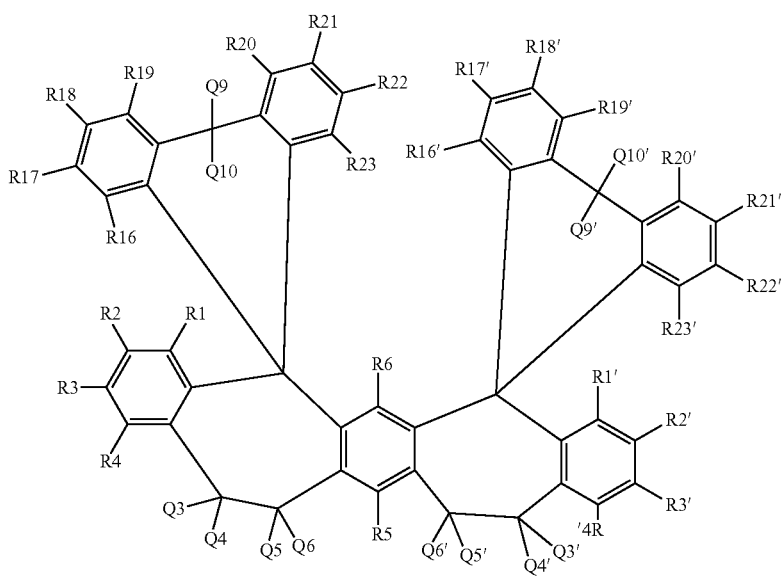

Formula XV

Formula XVI

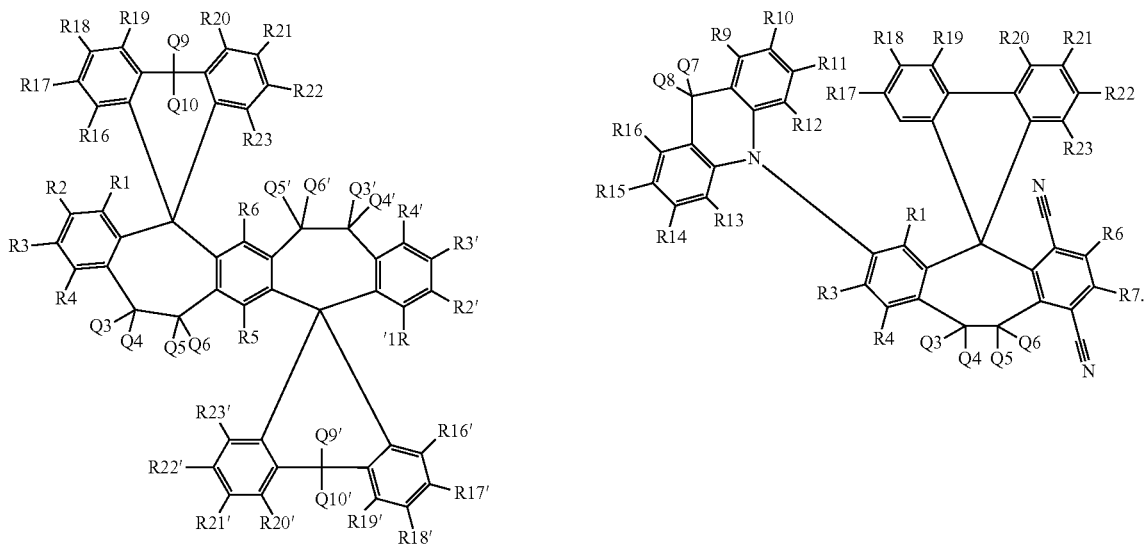

11. Optoelectronic device of claim 1, wherein the hydrogen atoms in one, several or in all positions of the organic molecule are replaced by deuterium.

12. An organic molecule comprising a structure or consisting of a structure according to a formula selected from the group consisting of:

formula Ia

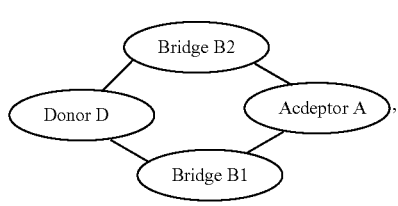

-continued

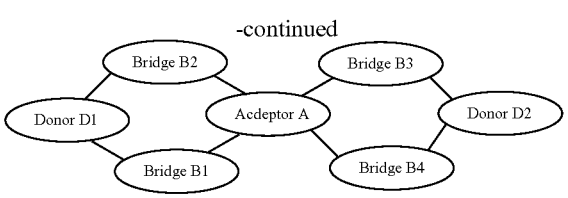

formula Ib the organic molecule includes:
an aromatic or hetero-aromatic donor member Donor D or aromatic or hetero-aromatic donor members Donor D1 and Donor D2, wherein each donor member is substituted with electron-donating or -withdrawing substituents, and
two or four non-conjugated bridge members selected from Bridge B1, Bridge B2, Bridge B3 and Bridge B4 bound to aromatic or hetero-aromatic acceptor segment Acceptor A that is substituted with electron-donating or -withdrawing substituents, and the bridge members Bridge B1, Bridge B2, Bridge B3, Bridge B4 are chosen such that there is a prevention of overlap between a HOMO of the donor segment and a LUMO of the acceptor segment,
wherein the hydrogen atoms in one, several or in all positions of the organic molecule of the abovementioned formulas are replaced by deuterium.

13. A method of emitting light, comprising emitting light from the organic molecule of claim 12, wherein the emitting light is from an emitter layer of an optoelectronic device having the organic molecule.

14. A process for preparing an optoelectronic device, wherein an organic molecule of claim 12 is used.

15. An optoelectronic device of claim 1, wherein:
the optoelectronic device is selected from the group consisting of organic light emitting diodes (OLEDs), light emitting electrochemical cells (LEECs or LECs), OLED sensors, non-hermetically shielded gas and vapor sensors, optical temperature sensors, organic solar cells (OSCs), organic field effect transistors, organic lasers, organic diodes, organic photodiodes and "down conversion" systems.

16. An optoelectronic device of claim 2, wherein an emission decay time of the organic molecule is less than 2 microseconds.

17. An opto-electronic device of claim 16, wherein the emission is not a TADF emission.

18. An opto-electronic device of claim 3, wherein the emission is not a TADF emission.

19. An optoelectronic device of claim 2, wherein the $^1CT \to S_0$ fluorescence with a substantially isoenergetic charge transfer triplet ($^3CT$) equilibrated state fluorescence from the $^1CT$ is singlet.

20. The organic molecule of claim 12, comprising a structure or consisting of a structure according to a formula selected from the group consisting of:

Formula IIa

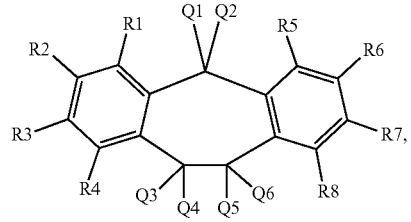

Formula IIb

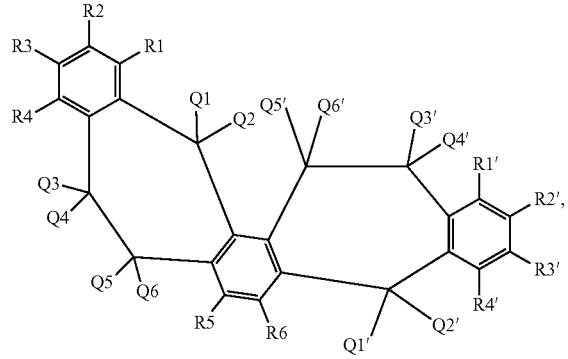

Formula IIc

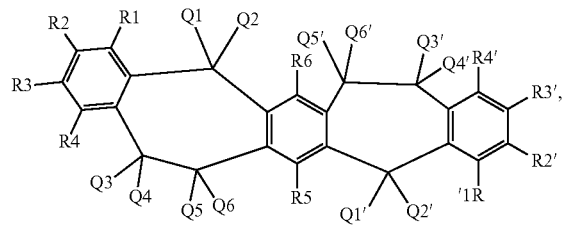

Formula IId

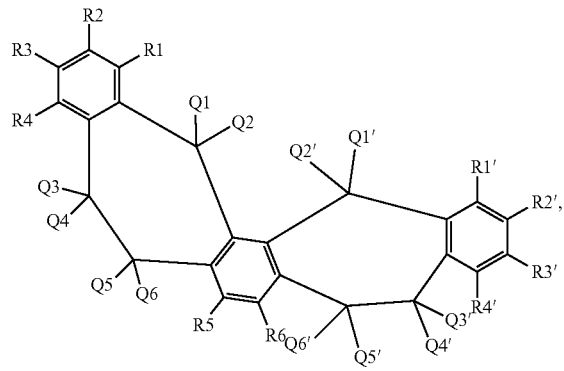

Formula IIe

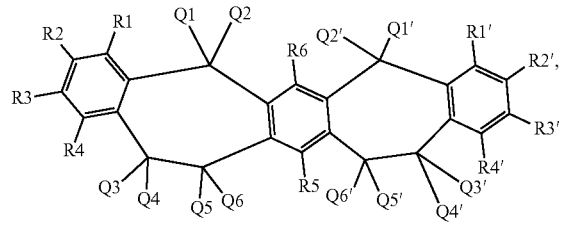

-continued
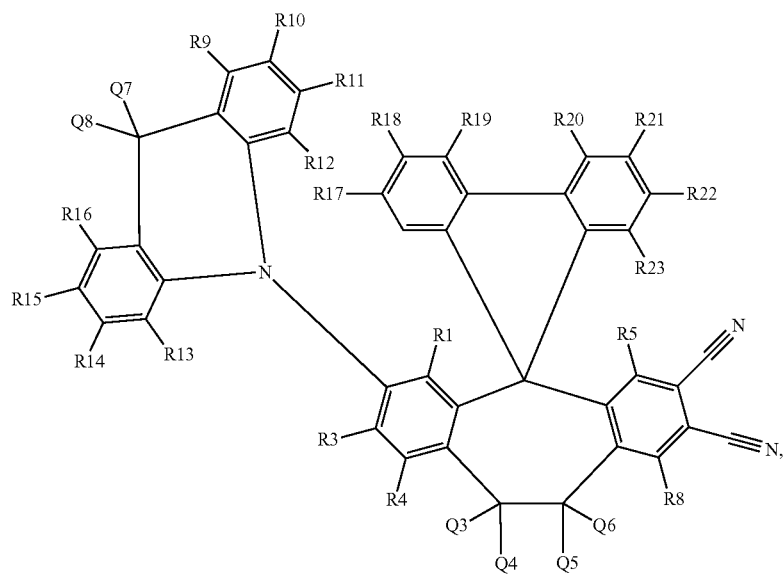
Formula IVa
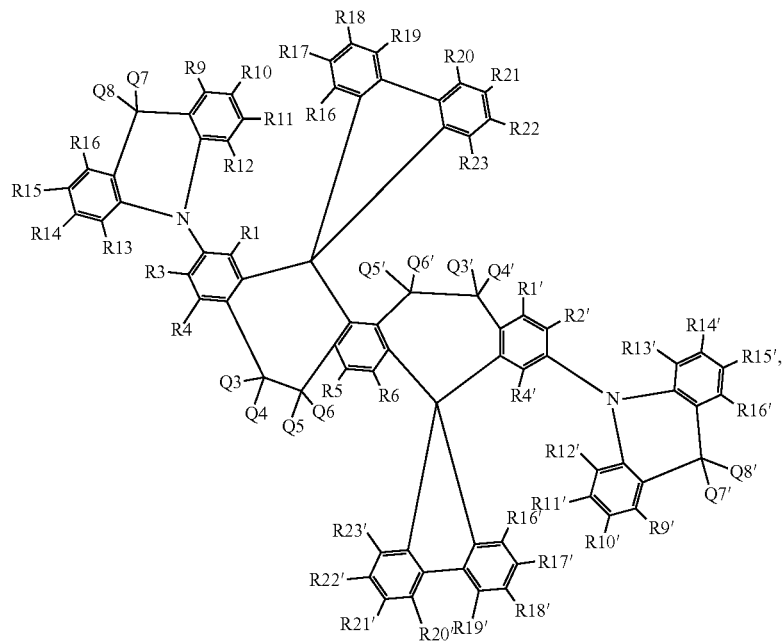
Formula IVb

-continued
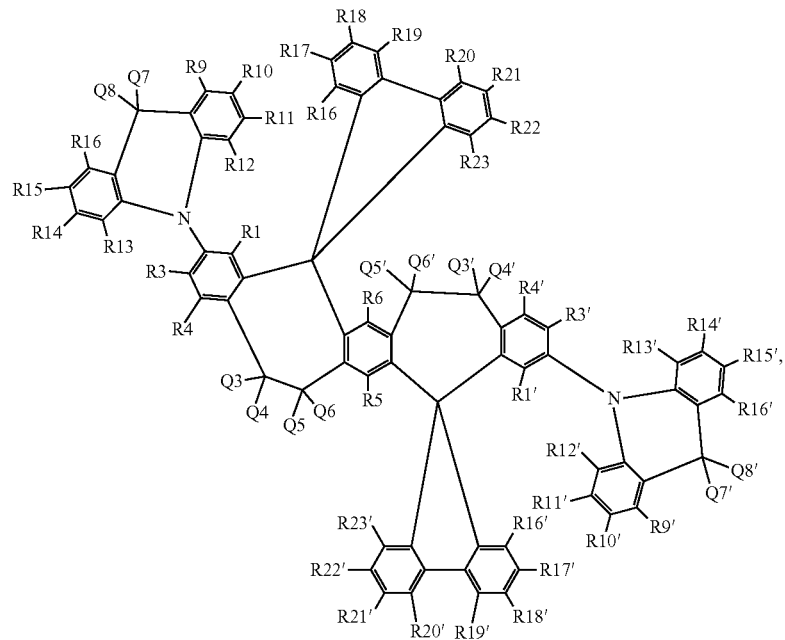
Formula IVc
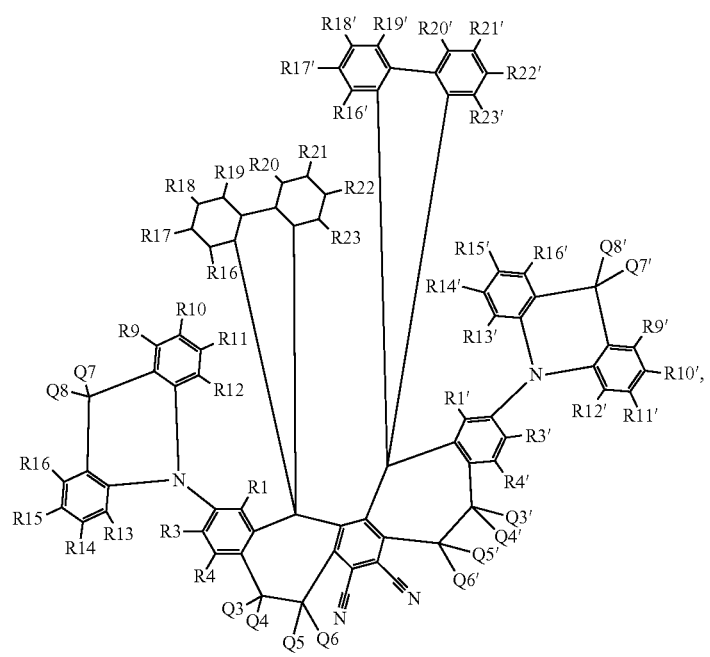
Formula IVd

Formula V
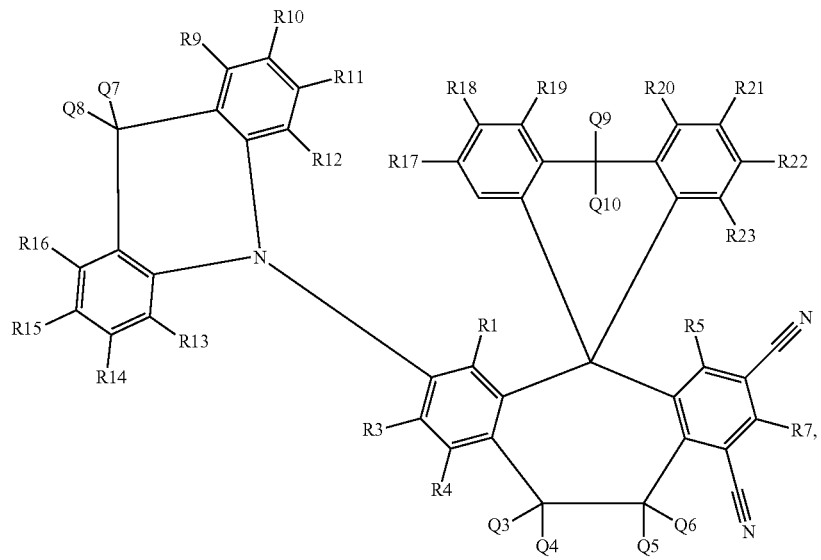
Formula VI
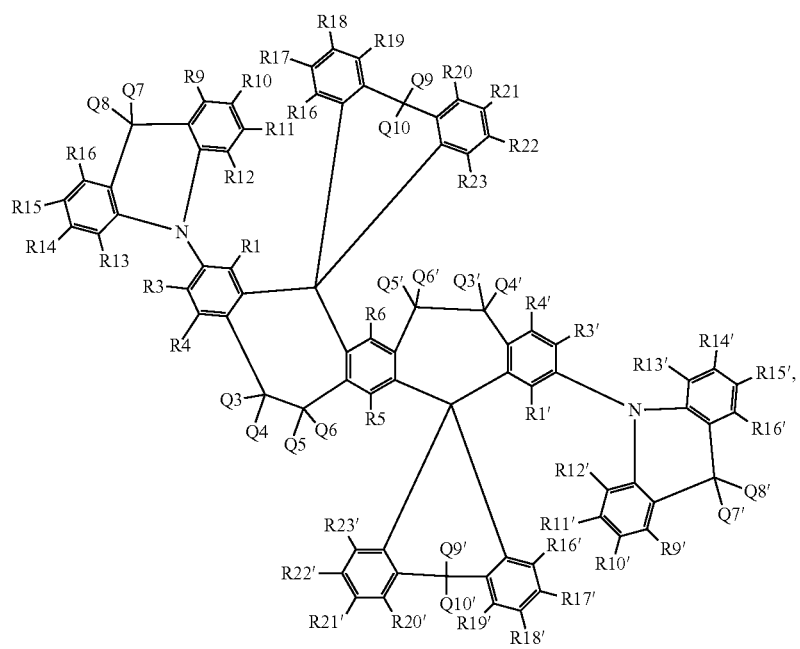

-continued
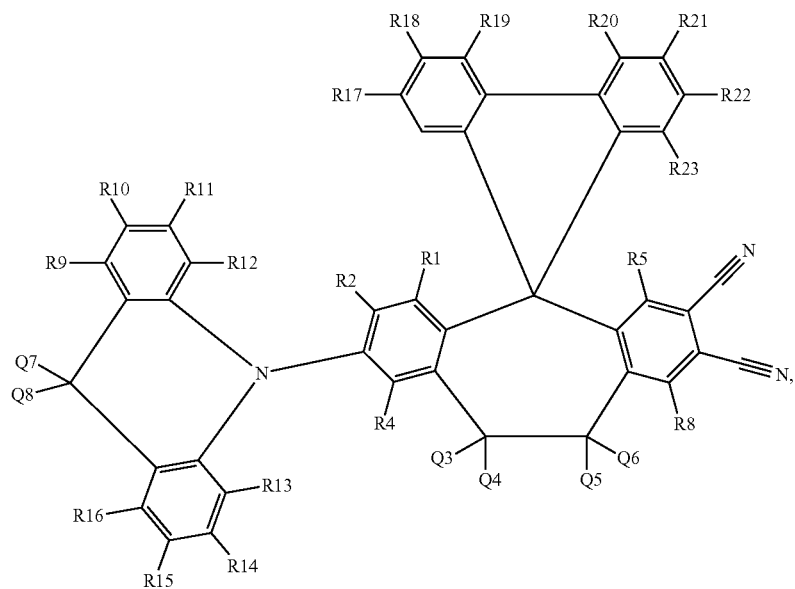
Formula VII
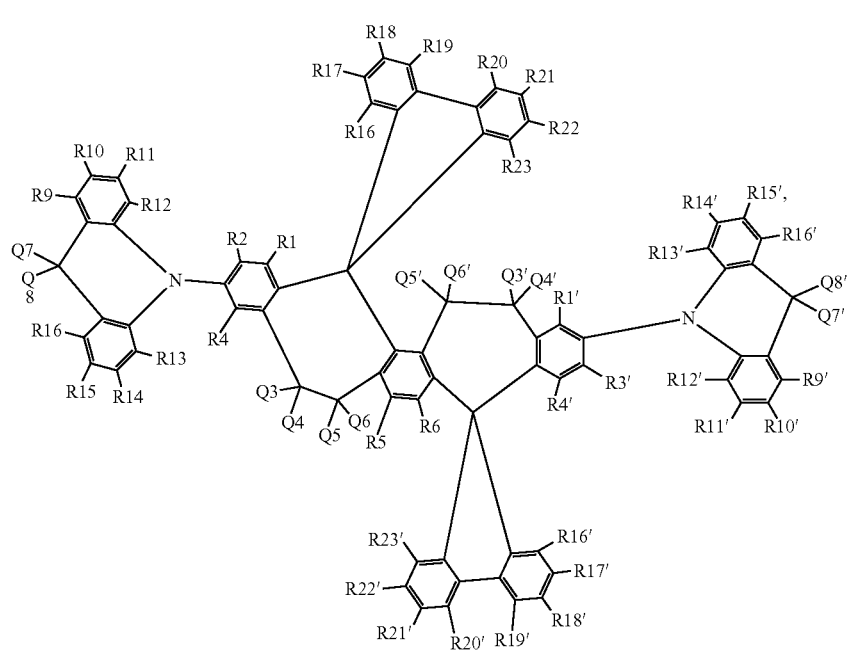
Formula VIII

-continued
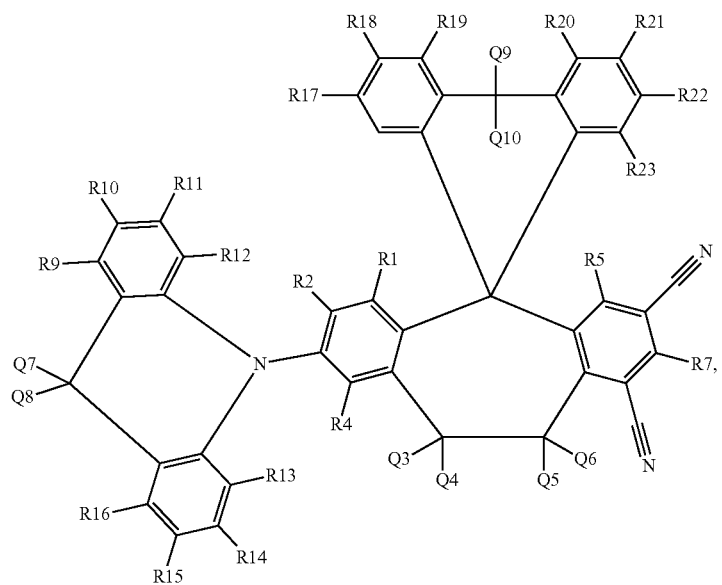
Formula IX
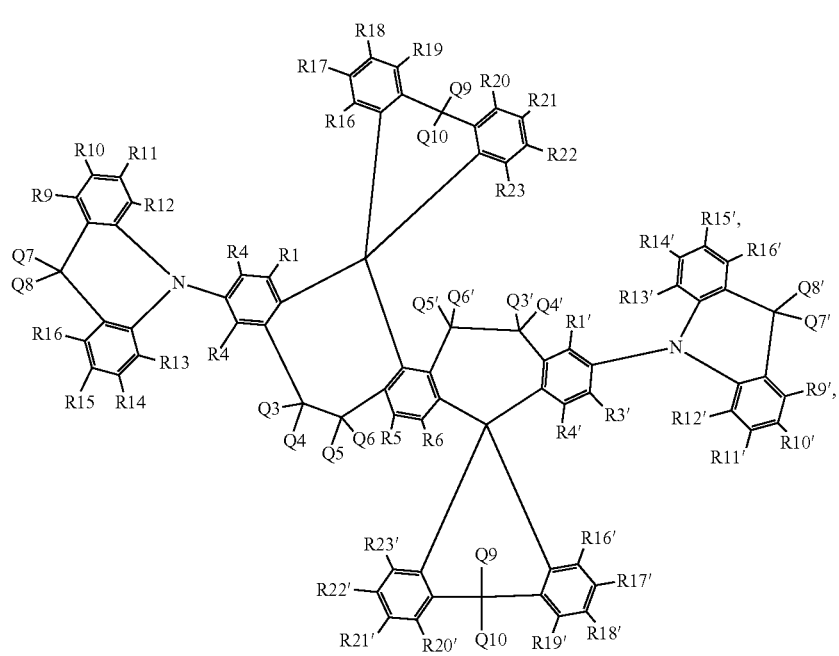
Formula X

Formula XI
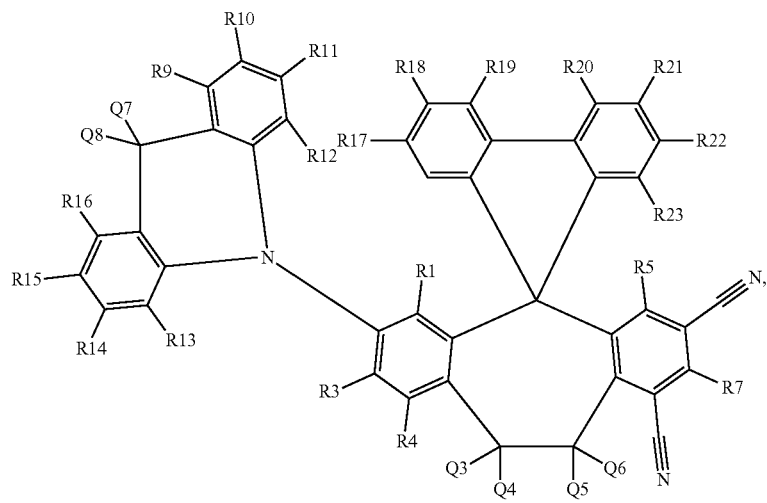
Formula XII
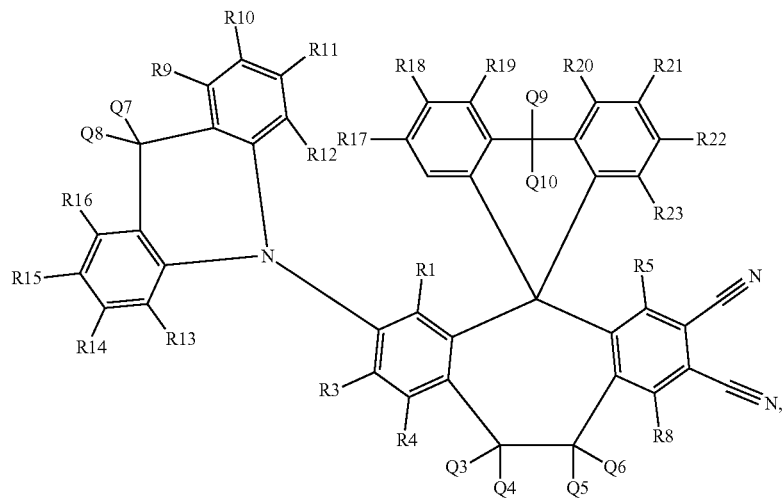
Formula XIII
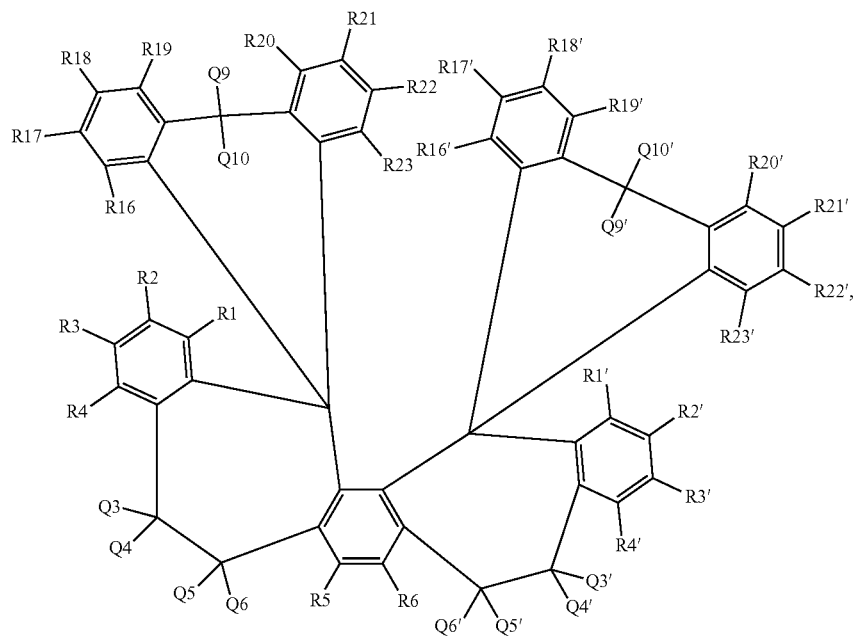

Formula XIV
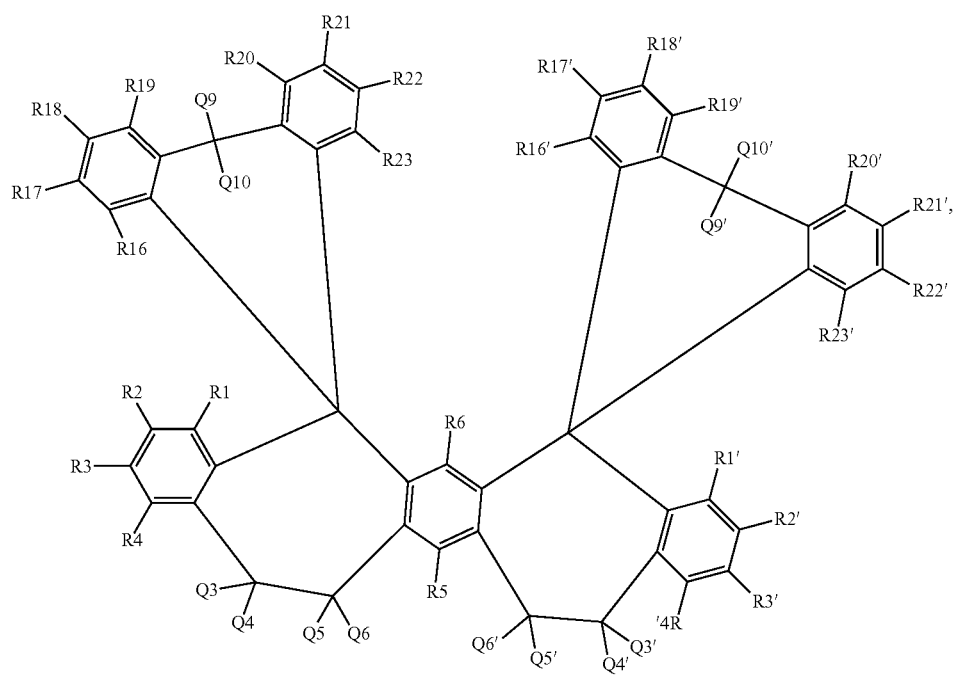
Formula XV
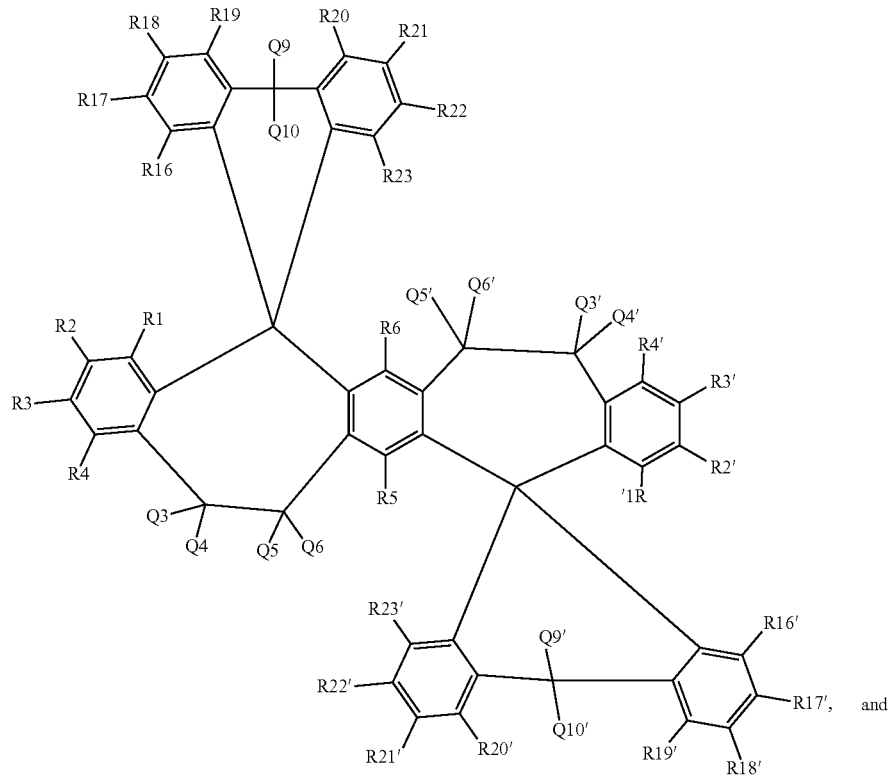
and

-continued

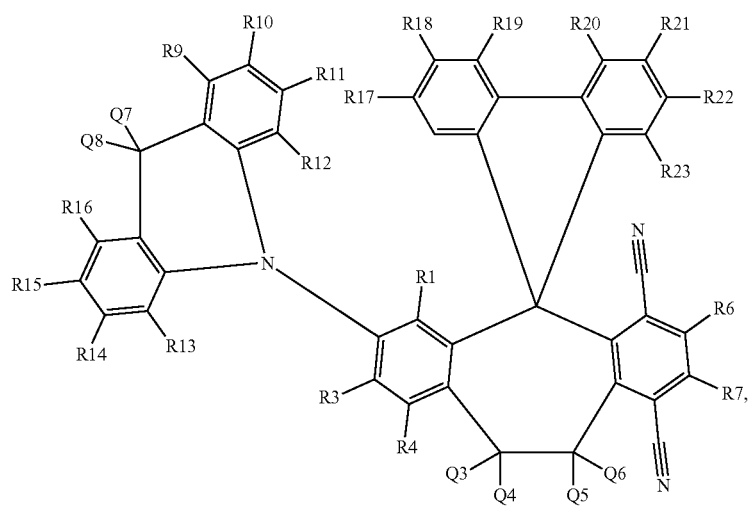

Formula XVI wherein the hydrogen atoms in one, several or in all positions of the organic molecule of the abovementioned formulas are replaced by deuterium;

wherein:
the 2,3: 6,7-dibenzosuberane backbone is substituted so the electronic properties of the aromatic ring systems are modified, the bridge members include:
Q1, Q2, and Q1' Q2' are independently selected from the group consisting of alkyl, alkenyl, alkynyl, cycloalkyl and aryl; and
Q3 to Q6 and Q3' to Q6' are independently selected from the group consisting of H, alkyl, alkenyl, alkynyl, cycloalkyl and aryl;

wherein:
Alkyl is a straight-chain (unbranched) or branched ($C_1$-$C_{10}$) alkyl having 1 to 10 carbon atoms in the main hydrocarbon chain,
Alkenyl is a straight or branched ($C_1$-$C_{10}$) alkenyl having 1 to 10 carbon atoms in the main hydrocarbon chain,
Alkynyl is a straight or branched ($C_1$-$C_{10}$) alkynyl having 1 to 10 carbon atoms in the main hydrocarbon chain,
Cycloalkyl is a ($C_3$-$C_7$) -cycloalkyl having 3 to 7 ring carbon atoms, and
Aryl is a 5-membered ring or 6-membered ring aromatic or heteroaromatic group,
"main hydrocarbon chain" used herein is the longest chain of the branched or non-linear alkyl, alkenyl or alkynyl;

wherein:
each group Q1 to Q6 and Q1' to Q6' independently may be substituted or unsubstituted with one or more F, Cl, Br, alkoxyl, thioalkoxyl, amine, silane, phosphine, borane, or aryl;
the groups Q1 and Q2, Q3 and Q4 groups, the groups Q5 and Q6, the groups Q1' and Q2', the groups Q3' and Q4', as well as the groups Q5' Q6' and are optionally chemically linked together to form other ring systems;

the donor members include:
R1 to R4 and R1' to R4' are independently selected from the group consisting of H, alkyl, alkenyl, alkynyl, cycloalkyl, alkoxyl, thioalkoxyl, amine, phosphine, silane, borane, fluorine, chlorine, bromine, or an Akr group defined by Formula IIIa or Formula IIIb,

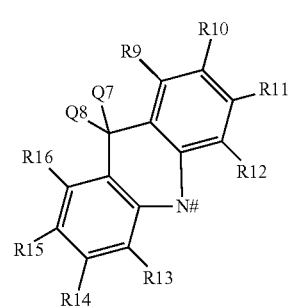

Formula IIIa

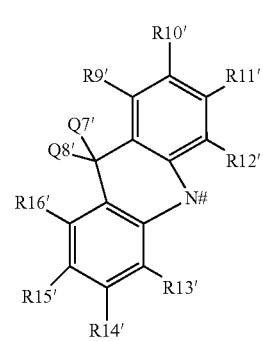

Formula IIIb in Formula IIa, at least one of R1 to R4 is independently the Akr group;
in Formulae IIb to IIe at least one of R1 to R4 is independently the Akr group and at least one of R1' to R4' is independently the Akr group, wherein:
Alkyl is a straight or branched ($C_1$-$C_{10}$) alkyl having 1 to 10 carbon atoms in the main hydrocarbon chain,
Alkenyl is a straight or branched ($C_1$-$C_{10}$) alkenyl having 1 to 10 carbon atoms in the main hydrocarbon chain, Alkynyl is a straight or branched ($C_1$-$C_{10}$) alkynyl, having 1 to 10 carbon atoms in the main hydrocarbon chain, Cycloalkyl is a ($C_3$-$C_7$)-cycloalkyl having 3 to 7 ring carbon atoms, and Aryl is a 5-membered ring or 6-membered ring aromatic or heteroaromatic group, wherein the alkoxyl, thioalkoxyl, amine, phosphine, silane and borane is in each case an alkoxyl OR', SR' thioalkoxyl, amine NR'R", phosphine PR'R", silane SiR'R"R"' and borane BR'R" wherein R', R" and R"' is independently a straight or branched ($C_1$-$C_{10}$) alkyl, ($C_1$-$C_{10}$)-alkene, ($C_1$-$C_{10}$) alkyne, ($C_3$-$C_7$) cycloalkyl or a 5-membered ring or 6-membered ring aromatic or heteroaromatic group;

wherein:

marks the point through which the Akr group is connected to the rest of the molecule, R9 to R16 and R9' to R16' are independently selected from H, ($C_1$-$C_{10}$) alkyl, ($C_1$-$C_{10}$)-alkenyl, ($C_1$-$C_{10}$)-alkynyl, ($C_3$-$C_7$) cycloalkyl, alkoxyl OR', amine NR'R", phosphine PR'R", silane SiR'R"R"', borane BR'R", fluorine, chlorine, bromine, or aryl, wherein the R', R" and R"' is a straight or branched ($C_1$-$C_{10}$) alkyl, ($C_1$-$C_{10}$) alkene, ($C_1$-$C_{10}$) alkyne, ($C_3$-$C_7$) cycloalkyl or a 5-membered ring or 6-membered ring aromatic or heteroaromatic group;

Q7, Q8, and Q7' Q8' are defined as Q1 to Q6 and Q1' to Q6' and may be linked together to form a further ring system;

the acceptor segment includes:

R5 to R8 are independently selected from H, $CH_3$, CN, COR', CO (OR'), CO (NR'R"), $SO_2$R', $SO_2$(OR'), SOR', $CF_3$, $CF_2$R', wherein R' and R" are straight or branched ($C_1$-$C_{10}$) alkyl, ($C_1$-$C_{10}$) alkene, ($C_1$-$C_{10}$) alkyne, ($C_3$-$C_7$) cycloalkyl or a 5-membered ring or 6-membered ring aromatic or heteroaromatic group, and at least one group is not H or $CH_3$;

wherein in the formula IIa, at least two substituents selected from R5, R6, R7 and R8 are not H or $CH_3$;

wherein R17 to R23 and R17' to R23' are defined as the R9 to R16 and R9' to R16'; and wherein Q9 and Q10 and Q9' and Q10' are defined as Q1 to Q8 and Q1' to Q8' and are optionally linked to one another so that a further ring system is formed.

\* \* \* \* \*